US009044351B2

(12) United States Patent
Wang et al.

(10) Patent No.: US 9,044,351 B2
(45) Date of Patent: Jun. 2, 2015

(54) IMPLANT AND DELIVERY SYSTEM WITH MULTIPLE MARKER INTERLOCKS

(75) Inventors: Lixiao Wang, Long Lake, MN (US); Jianlu Ma, Maple Grove, MN (US); Joe Tatalovich, St. Louis Park, MN (US); Peggy Waltz, Elk River, MN (US); Keith Smythe, Champlin, MN (US); Rich Kusleika, Eden Prairie, MN (US)

(73) Assignee: Covidien LP, Mansfield, MA (US)

(*) Notice: Subject to any disclaimer, the term of this patent is extended or adjusted under 35 U.S.C. 154(b) by 1622 days.

(21) Appl. No.: 11/748,235

(22) Filed: May 14, 2007

(65) Prior Publication Data

US 2007/0293930 A1 Dec. 20, 2007

Related U.S. Application Data

(60) Provisional application No. 60/891,596, filed on Feb. 26, 2007, provisional application No. 60/869,172, filed on Dec. 8, 2006, provisional application No. 60/800,106, filed on May 12, 2006.

(51) Int. Cl.

| | |
|---|---|
| ***A61F 2/06*** | (2013.01) |
| ***A61F 2/91*** | (2013.01) |
| ***A61F 2/915*** | (2013.01) |
| ***A61F 2/95*** | (2013.01) |
| *A61F 2/966* | (2013.01) |

(52) U.S. Cl.

CPC . *A61F 2/91* (2013.01); *A61F 2/915* (2013.01); *A61F 2/95* (2013.01); *A61F 2002/91541* (2013.01); *A61F 2002/91558* (2013.01); *A61F 2002/91591* (2013.01); *A61F 2002/9665* (2013.01); *A61F 2250/0098* (2013.01); *A61F 2220/005* (2013.01); *A61F 2220/0058* (2013.01); *A61F 2230/0054* (2013.01)

(58) Field of Classification Search

CPC ............. A61F 2/91; A61F 2/915; A61F 2/95; A61F 2002/91541; A61F 2002/91591; A61F 2002/9665; A61F 2250/0098; A61F 2220/005; A61F 2220/0058; A61F 2230/0054

USPC ..................... 623/1.11, 1.12, 1.13, 1.15, 1.23

See application file for complete search history.

(56) References Cited

U.S. PATENT DOCUMENTS 4,655,771 A * 4/1987 Wallsten ..................... 623/1.22
4,731,079 A 3/1988 Stoy
5,026,377 A 6/1991 Burton et al.

(Continued)

FOREIGN PATENT DOCUMENTS

EP 0699087 3/1996
EP 1 180 003 B1 11/2000

(Continued)

OTHER PUBLICATIONS

European Search Report from EP 10 19 5028 mailed Nov. 13, 2012.

*Primary Examiner* — Victor Nguyen
*Assistant Examiner* — Kevin Everage
(74) *Attorney, Agent, or Firm* — Alana T. Bergman, Esq.

(57) ABSTRACT

An implant delivery system has one or more interlock assemblies which connect the implant delivery catheter to the implant, an improved inner tubular member and an outer tubular member. The interlock assemblies, improved inner tubular member and outer tubular member cooperate to place the implant in tension during deployment, thereby reducing implant deployment force.

17 Claims, 18 Drawing Sheets

(56) References Cited

U.S. PATENT DOCUMENTS

| | | | | |
|---|---|---|---|---|
| 5,702,418 | A | 12/1997 | Ravenscroft | |
| 6,120,522 | A | 9/2000 | Vrba et al. | |
| 6,607,551 | B1 | 8/2003 | Sullivan et al. | |
| 6,899,730 | B1 | 5/2005 | Rivelli, Jr. | |
| 7,033,385 | B2 | 4/2006 | Eder et al. | |
| 7,172,617 | B2 | 2/2007 | Colgan | |
| 2003/0033001 | A1 | 2/2003 | Igaki | |
| 2004/0106977 | A1 | 6/2004 | Sullivan et al. | |
| 2004/0204749 | A1 | 10/2004 | Gunderson | |
| 2004/0236406 | A1 | 11/2004 | Gregorich | |
| 2005/0090834 | A1 * | 4/2005 | Chiang et al. | 606/108 |
| 2005/0125050 | A1 | 6/2005 | Carter et al. | |
| 2006/0206187 | A1 | 9/2006 | Parker et al. | |

FOREIGN PATENT DOCUMENTS

| | | |
|---|---|---|
| EP | 1 157 673 | 11/2001 |
| EP | 1223891 | 7/2002 |
| WO | WO 98/56315 | 12/1998 |
| WO | WO 00/71058 | 11/2000 |
| WO | WO 02/067782 | 9/2002 |
| WO | WO 2006/026377 | 3/2006 |

* cited by examiner

IMPLANT AND DELIVERY SYSTEM WITH MULTIPLE MARKER INTERLOCKS

FIELD OF THE INVENTION

The present invention relates to a system for delivering an implant to a site in a body lumen. More particularly, this invention pertains to a delivery system for a vascular implant such as a self-expanding stent.

BACKGROUND OF THE INVENTION

Stents are widely used for supporting a lumen structure in a patient's body. For example, a stent may be used to maintain patency of a carotid artery, coronary artery, other blood vessel or other body lumen such as the ureter, urethra, bronchus, esophagus, or other passage. A stent is typically a metal, tubular structure, although polymer stents are known. Stents can be permanent enduring implants, or can be bioabsorbable at least in part. Bioabsorbable stents can be polymeric, bio-polymeric, ceramic, bio-ceramic, metallic, or other materials and stents may elute over time substances such as drugs.

In certain stent designs, the stent is an open-celled tube that is expanded by an inflatable balloon at the deployment site. Another type of stent is of a "self-expanding" type. A self-expanding stent does not use a balloon or other source of force to move from a collapsed state to an expanded state. A self-expanding stent is passed through the body lumen in a collapsed state. At the point of an obstruction, or other deployment site in the body lumen, the stent is expanded to its expanded diameter for its intended purpose. An example of a self-expanding stent is a coil structure that is secured to a stent delivery device under tension in a collapsed state. At the deployment site, the coil is released so that the coil can expand to its enlarged diameter. Coil stents can be manufactured using a variety of methods, such as winding of wire, ribbon, or sheet on a mandrel or by laser cutting from a tube, followed by the appropriate heat treatments. Other types of self expanding stents are closed-cell or open-celled tubes made from a self-expanding material, for example, the Protégé GPS stent from ev3, Inc. of Plymouth, Minn. Cellular tube stents are commonly made by laser cutting of tubes, or cutting patterns into sheets followed by or preceded by welding the sheet into a tube shape, and other methods. The shape, length and other characteristics of a stent are typically chosen based on the location in which the stent will be deployed.

Conventional stents generally are comprised of struts or wires having openings therebetween. Some workers in the field have added coverings to stents and thereby substantially occluded the stent openings. Examples of such devices include covered stents, stent-grafts, and mesh covered stents. Generally speaking, covered stents and stent-grafts can be used as conduits for fluids in situations where little or no fluid loss through the wall of the conduit is desirable. Generally speaking, mesh covered stents can be used to maintain a luminal diameter large enough to permit flow in the conduit yet prevent liberation of emboli from the wall of the lumen into the lumen.

One delivery technique for a self expanding device such as a stent, covered stent, stent graft, or mesh covered stent is to mount the collapsed device on a distal end of a device delivery system. Such a system can be comprised of an outer tubular member and an inner tubular member. The inner and outer tubular members are axially slideable relative to one another. The device (in the collapsed state) is mounted surrounding the inner tubular member at its distal end. The outer tubular member (also called the outer sheath) surrounds the device at the distal end. One or more portions of the device are releasably attached to the inner tubular member by means of interlock assemblies and the interlock assemblies facilitate proper positioning and control of the device during device deployment.

Prior to advancing the device delivery system through the body lumen, a guide wire is first passed through the body lumen to the deployment site. The inner tube of the delivery system is hollow throughout at least a portion of its length such that it can be advanced over the guide wire to the deployment site. The combined structure (i.e., device mounted on device delivery system) is passed through the patient's lumen until the distal end of the delivery system arrives at the deployment site within the body lumen. The deployment system should have good bending flexibility in order to traverse tortuous vessels encountered during system advancement to a treatment site, and the device may include radiopaque markers to permit a physician to visualize positioning of the device under fluoroscopy prior to deployment. At the deployment site, the outer sheath is retracted to expose the device. The exposed device is free to self-expand within the body lumen. Following expansion of the device, the inner tube is free to pass through the device such that the delivery system can be removed through the body lumen leaving the device in place at the deployment site.

In prior art devices very high forces can be required to slide the inner and outer tubular members relative to one another and thereby deploy the device. This is especially true when attempting to deploy, for example, long devices, devices with a large amount of expansile force when compressed in a sheath, or bulky devices compressed into small sheaths in tortuous vessels.

What is needed is a system that permits low deployment force of long devices, devices with a large amount of expansile force when compressed in a sheath, or devices compressed into small sheaths in tortuous vessels.

In addition, in prior art devices, the stent may prematurely deploy as the outer tube is retracted. Namely, with the outer tube partially retracted, the exposed portion of the stent may expand resulting in the remainder of the stent being squeezed out of the outer tube. This can result in the stent being propelled distally beyond a desired deployment site. Also, once the stent is partially unsheathed, it is sometimes determined that the stent placement needs to be adjusted. With some existing systems, this is difficult since the stent has a tendency to force itself out of the sheath thereby making adjustments difficult. Further, once the stent has been deployed, subsequent adjustment of the stent deployment location can be difficult because re-sheathing typically cannot be readily accomplished. To overcome some of these problems some stent delivery systems are comprised of interlocks on the stent and on the inner member. See for example U.S. Pat. No. 6,814,746 to Thompson et. al., entitled "Implant Delivery System With Marker Interlock", and U.S. Pat. No. 6,623,518 to Thompson et. al., entitled "Implant Delivery System With Interlock", the contents of both included herein in their entirety by reference.

While interlocks on stents and stent delivery systems have improved the precision with which some stents can be delivered to treatment sites, it has been found that certain types of stents are not effectively delivered even by the existing interlock systems. For example, long stents, thin stents, or stents with a large amount of expansile force, when compressed in a sheath, tend to buckle along their length as the outer sheath is withdrawn from the inner tubular member. Stents with high axial flexibility parallel to the central axis of the stent can also be very difficult to deploy, and to deploy precisely, with the existing interlock systems. Visualization of these stents during deployment, particularly of the long stents, is often inadequate. These types of stents can also be difficult to load into the stent delivery system as well.

What is needed is a system that permits easy loading, precise delivery, and good visualization during deployment of long stents, thin stents, stents with a large amount of expansile force, and stents with high axial flexibility.

SUMMARY OF THE INVENTION

An implant delivery system comprises one or more interlock assemblies which connect the implant delivery catheter to the implant, an improved inner tubular member and an outer tubular member. A distal interlock assembly prevents axial movement of the implant relative to the inner member during deployment. The improved inner tubular member is reinforced or made of a material which is able to resist inward radial compressive forces thereon from the implant during deployment of the implant. The implant is frictionally engaged against the inner surface of the outer tubular member prior to deployment and as the outer tubular member is withdrawn proximally during deployment. The interlock assemblies, improved inner tubular member and outer tubular member cooperate to place the implant in tension during deployment, resulting in a decrease in the constrained diameter of the implant during deployment and a lengthening of the constraint length of the implant thereby reducing implant deployment force. A proximal interlock assembly accommodates any increases in the constrained length of the implant at the proximal end thereof which accompany decreases in the constrained diameter of the implant caused by the tensioning of the implant during deployment.

According to a one aspect of the present invention, system for delivering a medical device within a body lumen comprises: a tubular catheter having proximal and distal ends and comprising an outer shaft member slidably disposed about an inner shaft member; a medical device comprising a tubular, self-expanding section carried by the inner shaft member and disposed intermediate the inner shaft member and the outer shaft member, the implant having a length l and a constrained diameter d which frictionally engages an inner surface of the outer shaft member; and a tensioning mechanism for causing tensioning of the medical device when the outer shaft member moves relative to the inner shaft member. In another embodiment, the tensioning mechanism comprises a distal interlock structure carried by the inner member for preventing axial movement of a distal end of the implant when the outer sheath moves relative to the inner member. In another embodiment, at least a portion of the inner member is formed of a material able to resist compression forces exerted thereon by said implant. In yet another embodiment, the tensioning mechanism comprises a proximal interlock structure carried by the inner member and defining a receptacle for accommodating an increased length L of the implant when the outer sheath moves relative to the inner member. In still another embodiment, the tensioning mechanism comprises an inner surface of the outer sheath which frictionally engages at least a part of the implant when the outer sheath moves relative to the inner member.

According to a second aspect of the present invention, a medical device comprises: an implant having a proximal and distal end and a self-expanding portion with a constrained diameter d and constrained length l; and an implant delivery system comprising a tubular catheter having outer shaft sheath slidably disposed about an inner member; a mechanism for enabling increases in the constrained length l of the implant disposed intermediate the inner member and outer sheath when the outer sheath moves relative to the inner member.

According to a third aspect of the present invention, a medical device comprises: an implant having a proximal and a distal end and a self-expanding portion with a constrained diameter d and constrained length l; and an implant delivery system comprising a tubular catheter having outer shaft sheath slidably disposed about an inner member, a mechanism for decreasing the constrained diameter d of the implant disposed intermediate the inner member when the outer sheath moves relative to the inner member.

According to a fourth aspect of the present invention, method for deploying an implant comprises: a) providing an implant delivery system comprising an at least partially self expanding implant carried by an inner member and outer sheath slidably mounted over the inner member, the implant having a constrained length l and a constrained diameter d when disposed intermediate the inner member and the outer sheath; and b) placing the implant in tension while enabling axial movement of the outer sheath relative to the implant. In one embodiment, the implant delivery system further comprises a distal interlock structure carried by the inner member for engaging a portion of the implant and wherein b) further comprises: b1) resisting axial movement of a distal end of the implant relative to the inner member as the outer sheath moves relative to the inner member. In another embodiment, the implant delivery system further comprises at least a portion of the inner member formed of a material able to resist compression forces exerted thereon by said implant and wherein b) further comprises: b1) resisting radial compression of the implant on the inner member as the diameter of the implant is less than the constrained diameter d. In yet another embodiment, the implant delivery system further comprises an inner surface of the outer sheath and wherein b) further comprises b1) frictionally engaging at least a part of the implant with the inner surface of the outer sheath as the outer sheath moves relative to the inner member. In still another embodiment, the method further comprises: c) accommodating increases in the length l of the implant while resisting axial movement of the implant relative to the inner member as the outer sheath moves relative to the inner member. In yet a further embodiment, the implant delivery system further comprises a proximal interlock structure carried by the inner member and defining a receptacle for receiving an end of the implant. In still other embodiments, and wherein c) comprises: c1) receiving any increases in the length l of the constrained implant into the receptacle of the proximal interlock structure as the outer sheath moves relative to the inner member.

BRIEF DESCRIPTION OF THE DRAWINGS

The above and further advantages of the invention may be better understood by referring to the following description in conjunction with the accompanying drawings in which.

DETAILED DESCRIPTION

With reference now to the various drawing figures a description is provided of embodiments that are examples of how inventive aspects in accordance with the principles of the present invention may be practiced. It is to be understood that both the foregoing general description and the following detailed description are exemplary and explanatory only and are not restrictive of the broad inventive aspects disclosed herein. It will also be appreciated that the inventive concepts disclosed herein are not limited to the particular device configurations disclosed herein, but are instead applicable to any number of different device configurations.

Figure 1:
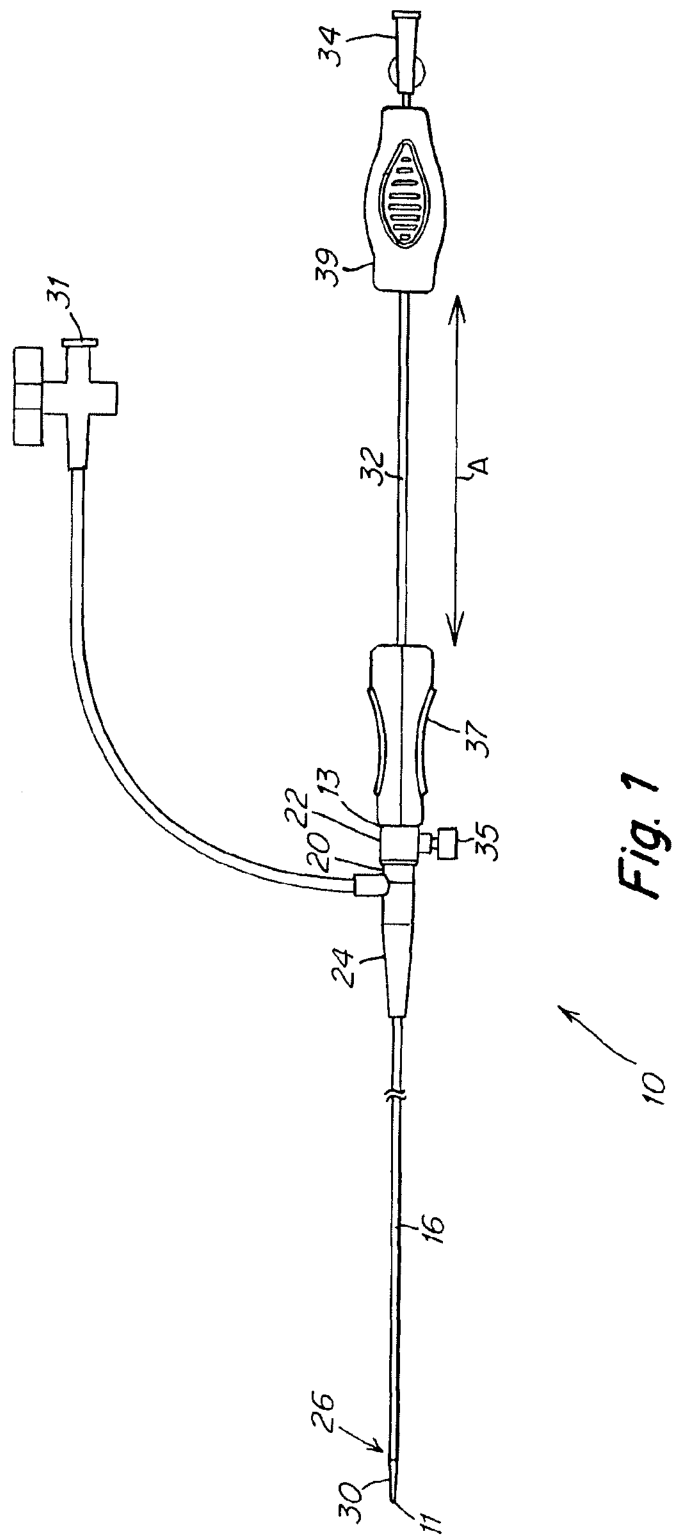
FIG. 1 illustrates a side elevation view of one embodiment of an implant delivery system having features that are examples of inventive aspects in accordance with the principles of the present disclosure.
Figure 2:
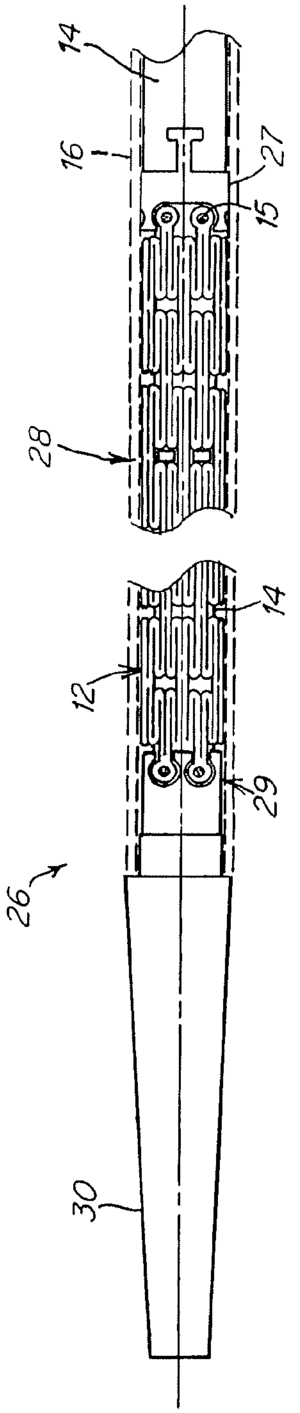
FIG. 2 illustrates an enlarged view of the distal end of the system of FIG. 1 with the outer sheath shown in phantom line.
Figure 3:
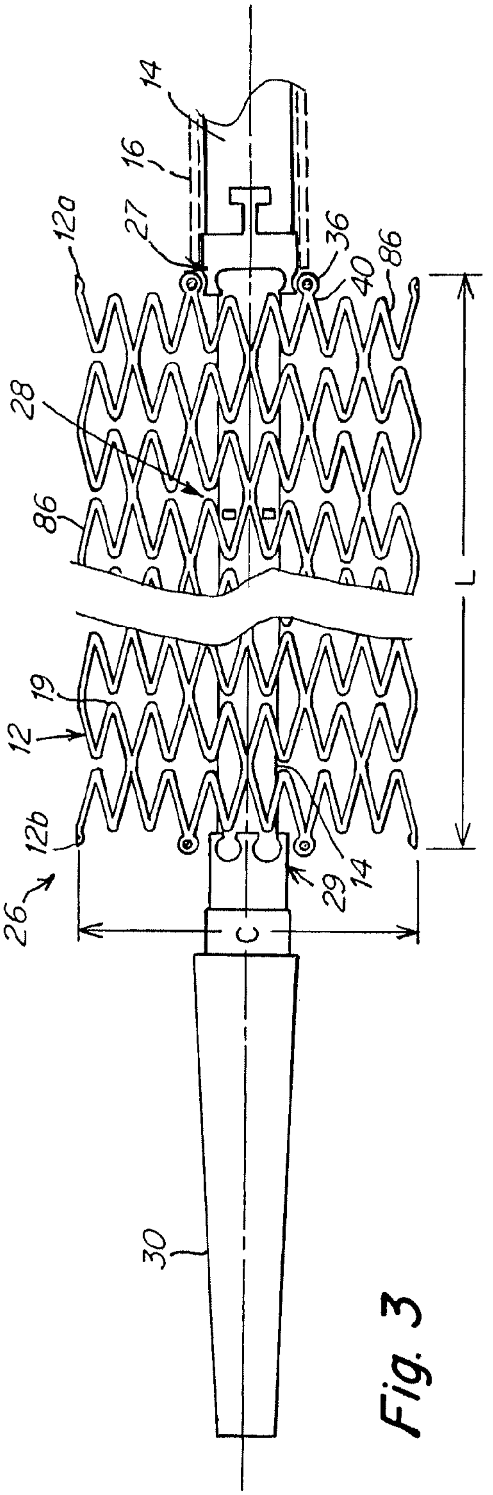
FIG. 3 illustrates the view of FIG. 2 with the outer sheath retracted.

FIGS. 1-3 show an over-the-wire device delivery system, in this example stent delivery system 10 having distal and proximal ends 11, 13, inner member 14, and retractable outer sheath 16 that slides over inner member 14. Stent mounting location 26 is located adjacent distal end 11 of system 10. Stent 12 (visible in FIGS. 2 and 3) is carried at stent mounting location 26 of stent delivery system 10 in a collapsed (or reduced diameter) state. Stent 12 mounts over inner member 14 and is covered by sheath 16 so as to be retained in the collapsed state (see FIG. 2). Stent 12 is released (i.e., deployed) by retracting sheath 16 to uncover or expose stent 12 (see FIG. 3). System 10 includes proximal interlock structure 27 that prevents stent 12 from prematurely deploying, one or more optional mid interlock structures 28 that assist with uniform stent deployment and with stent loading, and distal interlock structure 29 that assists with stent deployment and with stent loading. Upon release of stent 12 from stent delivery system 10, stent 12 expands to an enlarged diameter to abut against the walls of the patient's lumen in order to support patency of the lumen. The expansion of stent 12 also causes stent 12 to disengage from interlock structures 27, 28 and 29.

System 10 is configured to be advanced through the patients body lumen. In use, system 10 is preferably sufficiently long for distal end 11 to be placed at the deployment site in the patient's body lumen with proximal end 13 remaining external to the patient's body for manipulation by an operator.

Sheath 16 of system 10 may have a variety of different constructions. In one embodiment, the sheath has a tubular construction of braid-reinforced polyester adapted to resist kinking and to transmit axial forces along the length of sheath 16. Sheath 16 may be constructed so as to have varying degrees of flexibility along its length. Inner member 14 of system 10 is relatively flexible in bending and has good column strength. Construction and function of inner member 14 is described in further detail below. In one embodiment, inner member 14 has a tubular configuration and defines a lumen that extends through an entire length of inner member 14. This type of configuration allows the system to be passed over a guidewire for guiding the system to a desired deployment location. However, in other embodiments, inner member 14 can have a solid, non-tubular configuration.

Distal end 11 of system 10 includes a tapered and flexible distal tip member 30 that is sufficiently flexible to permit advancement of stent deployment system 10 through the patients lumen while minimizing trauma to the walls of the patient's lumen. Tip 30 is connected to inner member 14 adjacent stent mounting location 26. Proximal end 13 of system 10 includes manifold housing 20 connected to lock housing 22. Sheath 16 connects to manifold housing 20. Strain relief jacket 24 surrounds sheath 16 adjacent its connection to housing 20 to provide strain relief for sheath 16. Inner member 14 passes through both manifold housing 20 and lock housing 22. Outer reinforcing member 32 surrounds and is bonded to inner member 14 adjacent proximal end 13 of system 10. Reinforcing member 32 may be made of a relatively rigid material such as stainless steel. Port housing 34 is bonded to reinforcing member 32. Port housing 34 has a bore aligned with an inner lumen of inner member 14 and functions to facilitate access to the inner lumen.

Manifold housing 20 carries admission port 31 for injecting a contrast media into the interior of manifold housing 20. The interior of manifold housing 20 is in fluid communication with a passage between inner member 14 and sheath 16. In use, the contrast media can be directed from the passage into the patient's body lumen through discharge ports (not shown).

Lock housing 22 carries a threaded locking member (or lock nut) 35 which can be turned to engage reinforcing member 32. Lock nut 35 selectively permits and fixes axially movement between the inner member and sheath 16. Relative movement between the inner member and the sheath is permitted to define a transport position and a deploy position of the system 10.

First and second handles 37, 39 are secured to lock housing 22 and reinforcing member 32, respectively. In the transport position, handles 37 and 39 are spaced apart and sheath 16 covers stent mounting location 26 to prevent premature deployment of stent 12. When handles 37 and 39 are moved toward each other, sheath 16 slides rearwardly or proximally relative to inner member 14. In other words, relative axial movement between handles 37 and 39 (represented by arrow A) results in relative axial movement between inner member 14 and sheath 16. In particular, sheath 16 slides rearwardly from the transport position to the deploy position to fully expose stent mounting location 26 and permit stent 12 to freely expand toward its fully expanded diameter. After such expansion, the stent delivery system can be proximally withdrawn through the expanded stent and removed.

In one embodiment delivery system 10 is comprised of an interlock a configuration (e.g., interlock structures 27, 28, or 29 of FIGS. 2 and 3) that constrains relative axial movement between stent 12 and inner member 14 until after sheath 16 has been retracted. For example, when stent 12 is mounted on inner member 14 and restrained in the compressed orientation by sheath 16, a proximal interlock geometry located at a proximal end 12*a* of stent 12 interlocks with proximal interlock structure 27 adjacent the stent mounting location 26, a mid interlock geometry located at one or more locations along length of stent 12 interlocks with a mid interlock structure 28 adjacent the stent mounting location 26, and a distal interlock geometry located at a distal end 12*b* of stent 12 interlocks with a distal interlock structure 29 adjacent the stent mounting location 26. The interlock configurations remain interlocked to constrain axial movement of stent 12 until after the sheath has been retracted beyond a predetermined location (e.g., the proximal-most end 12*a* of stent 12). When sheath 16 has been retracted beyond the predetermined location, the interlock geometry of stent 12 is allowed to expand. As the interlock geometry of the stent expands, the interlock geometry of stent 12 disengages from the proximal, mid, and distal interlock structures thereby allowing inner member 14 of system 10 to be moved axially relative to the stent without interference from the interlock configurations.

Stent interlock structures 27, 28 and 29 are fixedly attached to inner member 14 adjacent mounting location 26. For example, stent interlock structures 27, 28 and 29 can be bonded, crimped, swaged, affixed, fastened, fused, molded in, embedded in, or otherwise secured to inner member 14. Some embodiments include stent-retaining structures having interlocks formed as an integral/unitary structure with the inner member. In other embodiments stent retainers in the form of separate pieces can be secured to inner member 14. For example, components can be machined, etched, stamped, formed, or otherwise fabricated into the surface of a ring of metal, engineering polymer, ceramic, or other material and the ring applied to the inner member by adhesive bonding, welding, solvent welding, fusing, or other techniques known in the art. In an alternate embodiment, stent interlock structures 27, 28 and 29 may be comprised of stent ends having cavities and retainers comprising interlocking enlarged ends and located adjacent stent mounting location 26 of stent delivery system 10. In other embodiment's stent interlock structures 27, 28 and 29 comprise opposing surfaces that mechanically interfere with proximal or distal movement of stent ends 12*a*, 12*b* along the lengthwise axis of the stent but which allow radial movement of stent ends 12*a*, 12*b*.

Figure 4A:
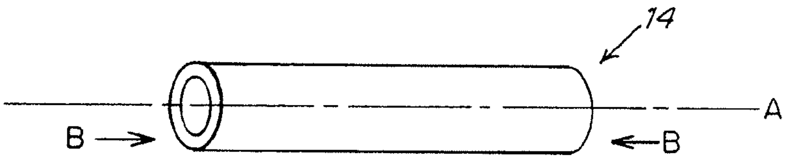
FIGS. 4A-4G illustrate portions of the system of FIG. 1.

Inner member 14, illustrated in FIG. 4A, is comprised of one or more materials having good flexibility when bent transverse to central axis A and high stiffness when compressed in direction of arrows B-B along central axis A. In contradistinction, prior art inner members, typically made of polymeric materials such as nylon, polyethylene, fluoropolymers, and other materials, have good flexibility when bent transverse to central axis A and but low stiffness when compressed in direction of arrows B-B along central axis A. Good flexibility when bent transverse to central axis A can be measured by standard 3 point bending tests. In one example, desirable stent delivery systems having a stent mounted thereon, measured in 3 point bending over the region comprising the compressed stent, have a peak force on the test force-displacement curve in the range of 75-200 grams. Inner member 14 may be comprised of crosslinked or non-crosslinked polymers that are extruded into the shape of tubing and then axially stretched to increase the relative orientation of the constituent polymer molecules along the axis A of the inner member. Inner member axial stretches from 100% to 1,000% are contemplated. In one embodiment inner member 14 is comprised of oriented polyester tubing having been axially stretched by 250% after extrusion. In another embodiment inner member 14 is comprised of oriented polyethylene tubing having been extruded, crosslinked, and axially stretched by 500% after crosslinking.

Figure 4B:
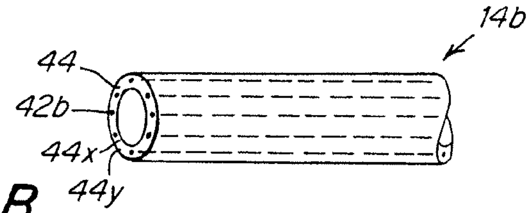
Figure 4C:
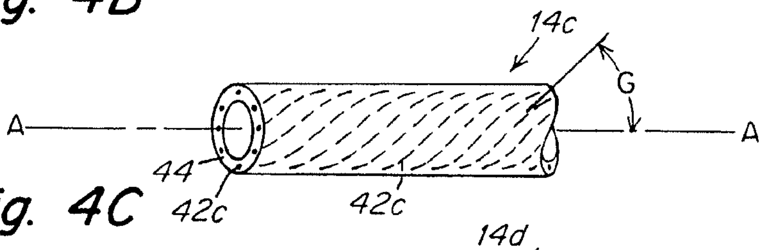

FIGS. 4A-4G illustrate examples of improved inner members. For clarity only one layer of reinforcement structures are shown (in phantom) in the Figures, and hidden lines for matrix components are not shown. FIG. 4B illustrates inner member 14*b* having reinforcing strands 42*b* embedded within matrix 44. Reinforcing strands 42*b* may be comprised of metal including but not limited to stainless steel, Elgiloy, superelastic alloys including Nitinol, gold, tantalum, tungsten, platinum, metallic glasses, and other metals; may be comprised of polymer including but not limited to PEEK, Liquid Crystal, polyester, Kevlar, polyamide, polyimide, and other polymers. The cross sectional shape of reinforcing strands 42*b* may be round, flat, ovoid, square, triangular, polygonal, irregular, or other shapes. Reinforcing strand maximum cross-sectional transverse dimensions from 0.0005" to 0.005" are contemplated. In one embodiment reinforcing strands are comprised of 0.001"×0.003" flat superelastic nitinol wire. In another embodiment reinforcing strands are comprised of 0.0015" diameter round stainless steel wire. Inner members 14*b* comprised of from 1 to 500 reinforcing strands are contemplated. In one embodiment inner member 14*b* is comprised of 4 reinforcing strands. In another embodiment inner member 14*b* is comprised of 24 reinforcing strands. One, two, three, or more layers of reinforcing strands may be used. Matrix 44 may be comprised of polymer including but not limited to thermoplastics, thermosets, polyethylene, polypropylene, fluoropolymers such as FEP or PTFE, PEEK, Liquid Crystal, polyester, Kevlar, polyamide, polyimide, and other polymers. Matrix 44 may be comprised of one or more layers, and the one or more layers may be bonded together. For example, FIG. 4C illustrates inner layer 44*x* and outer layer 44*y* bonded to each other and to reinforcing strands 42*c*. Some or all of matrix layers and reinforcing strands may be bonded to each other using adhesive, solvent, heat, ultrasonic vibration, laser energy, radiofrequency energy, or other means.

Reinforcing strands of improved inner member 14 can be configured in various ways and oriented in various directions relative to central axis A. FIG. 4B illustrates improved inner member 14*b* comprised of reinforcing strands 42*b* embedded in matrix 44. Reinforcing strands 42*b* are configured in the shape of straight strands and are oriented parallel to central axis A. Reinforcing strands 42*b* can vary in number and spacing according to the relative dimensions of inner member 14*b* and strands 42*b*. In one embodiment adjacent strands 42*b* are separated by spaces and in another embodiment at least some of strands 42*b* are in side to side contact along at least a portion of their length.

FIG. 4C illustrates improved inner member 14*c* comprised of reinforcing strands 42*c* embedded in matrix 44. Reinforcing strands 42*c* are configured in the shape of helical wound strands around central axis A. Angle G between helical wound strands 42*c* and central axis A is contemplated to be as low as 3 degrees and as high as 44 degrees. In one embodiment angle G between helical wound strands 42*c* and central axis A is between 10 and 35 degrees. In another embodiment angle G between helical wound strands 42*c* and central axis A is between 20 and 28 degrees. Reinforcing strands 42*c* can vary in number and spacing according to the relative dimensions of inner member 14*c* and strands 42*c*. In one embodiment adjacent strands 42*c* are separated by spaces and in another embodiment at least some of strands 42*c* are in side to side contact along at least a portion of their length.

Figure 4D:
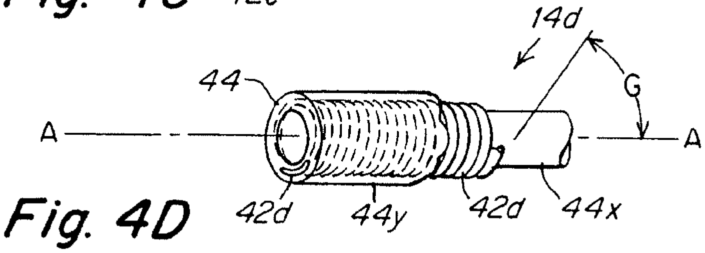
Figure 4E:
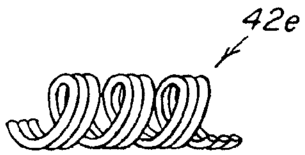

FIG. 4D illustrates improved inner member 14*d* comprised of reinforcing strands 42*d* embedded in matrix 44 comprised of inner layer 44*x* and outer layer 44*y* bonded to each other and to reinforcing strands 42*d*. Reinforcing strands 42*d* are configured in the shape of coil wound strands around central axis A. Angle G between coil wound strands 42*d* and central axis A is contemplated to be as low as 45 degrees and as high as 87 degrees. In one embodiment angle G between helical wound strands 42*d* and central axis A is between 50 and 75 degrees. In another embodiment angle G between helical wound strands 42*d* and central axis A is between 60 and 70 degrees. Reinforcing strands 42*d* can vary in number and spacing according to the relative dimensions of inner member 14*d* and strands 42*d*. In one embodiment adjacent strands 42*d* are separated by spaces and in another embodiment at least some of strands 42*d* are in side to side contact along at least a portion of their length. In another embodiment reinforcement strands 42*e* are comprised of multifilar windings as illustrated in FIG. 4E. In the example illustrated in FIG. 4E reinforcement strands 42*e* are comprised of a 3-filar winding.

Figure 4F:
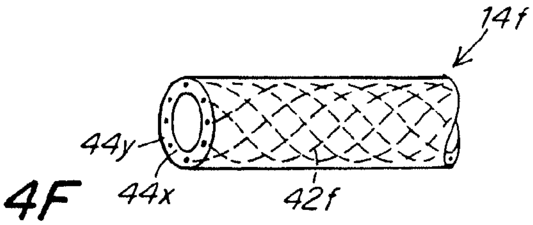

FIG. 4F illustrates improved inner member 14*f* comprised of reinforcing layer 42*f* embedded in matrix comprised of inner layer 44*x* and outer layer 44*y* bonded to each other and to reinforcing strands 42*f*. In one embodiment reinforcing layer 42*f* is configured in the shape of interwoven strands substantially concentrically arranged around central axis A. Reinforcing strands can vary in number and spacing according to the relative dimensions of inner member 14*f* and strands. Inner members comprised of from 3 to 72 reinforcing strands are contemplated. In one embodiment reinforcing layer 42*f* is comprised of 24 braided strands and in another embodiment reinforcing layer 42*f* is comprised of 48 braided strands. In one embodiment improved inner member 14*f* (0.380" inside diameter×0.045" outside diameter) is comprised of 0.001" thick polyimide inner layer, 0.0015" thick nylon 12 outer layer and 16 braided type 304V stainless steel reinforcing strands of 0.0005"×0.0030" flat wire with all 3 layers heat bonded to each other.

In another embodiment, reinforcing layer 42*f* may be comprised of tubes having holes, slots, or apertures formed therein, manufactured using processes such as etching, drilling, punching, laser cutting, electrodeposition, and other processes. One, two, three, or more concentric reinforcing layers may be used. In one embodiment, improved inner member reinforcement layer 42*f* may be comprised of structures illustrated and described in U.S. Pat. No. 6,290,692, entitled "Catheter Support Structure" in U.S. Pat. No. 6,273,876, entitled "Catheter Segments Having Circumferential Supports With Axial Projection", the contents of which are incorporated herein in their entirety by this reference for all purposes.

Figure 4G:
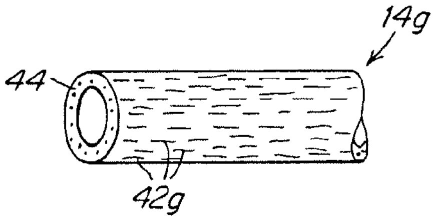

FIG. 4G illustrates improved inner member 14*g* comprised of a composite of reinforcing strands 42*g* embedded in matrix 44. Reinforcing strands 42*g* are configured in the shape of straight strands and are oriented parallel to central axis A. Strands 42*g*, commonly referred to as fiber reinforcements, have diameters ranging from 1 micron to 100 micron, and aspect ratio's (ratio of length to diameter) of between 5:1 and 50:1. In one embodiment improved inner member 14*g* is produced by blending polymer material matrix 44 with many thousands of strands 42*g* followed by extrusion or molding. Improved inner members 14*g* produced by blending polymer material matrix 44 with from 10,000 to 100,000,000 strands 42*g* over a cross section normal to the longitudinal axis of the inner member are contemplated.

Stent 12 has a length l and a circumference C, and includes a plurality of struts 86 (i.e., reinforcing members). At least some of the struts 86 have free terminal ends 40 that define proximal and distal ends 12*a* and 12*b* of stent 12. Stent 12 includes an interlock geometry in the form of enlargements 36 positioned at the free terminal ends of struts 86. As shown in FIG. 3, the enlargements are circular enlargements. It will be appreciated that other interlock shapes and configurations could also be used. Alternative interlock and marker interlock configurations useful within the scope of this invention are described within U.S. Patent Application No. 60/800,106, entitled "Implant And Delivery System With Multiple Marker Interlocks", the contents of which are incorporated herein in their entirety by this reference for all purposes. Enlargements 36 project outwardly from struts 86 in a circumferential direction (i.e. in a direction coinciding with the circumference C of stent 12). In one embodiment, stent 12 can be manufactured by cutting (e.g., laser cutting) the various features from a solid tube of material. When manufactured by this technique, enlargements 36 do not project radially beyond an inner and outer diameter of the stent.

Stent configurations suitable for the invention include but are not limited to cellular stents, fracturable stents, coil stents, covered stents, stent grafts, mesh covered stents, tapered stents, flared stents, braided stents, bifurcation stents, and other stents as are known in the art. Long stents are especially suited to the invention. Medical device delivery systems for stents having lengths of from 40-400 mm are contemplated. In one embodiment, a stent delivery system having improved inner member can deliver and deploy an 80 mm stent. In another embodiment, a stent delivery system having improved inner member can deliver and deploy a 120 mm stent. In another embodiment, a stent delivery system having improved inner member can deliver and deploy a 150 mm stent. In another embodiment, a stent delivery system having improved inner member can deliver and deploy a 180 mm stent. In another embodiment, a stent delivery system having improved inner member can deliver and deploy a 200 mm stent. In another embodiment, a stent delivery system having improved inner member can deliver and deploy a 250 mm stent. In another embodiment, a stent delivery system having improved inner member can deliver and deploy a 300 mm stent.

Figure 5A:
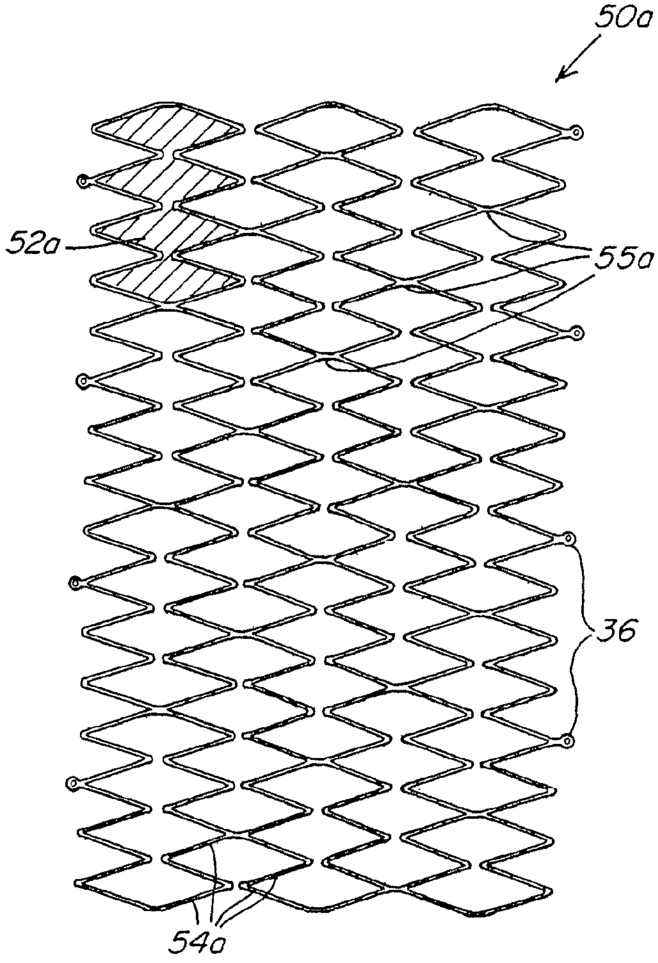
FIGS. 5A and 5B illustrate plan views of exemplar medical device embodiments having features in accordance with the principles of the present disclosure. The medical devices are shown expanded, cut longitudinally and laid flat.
Figure 5B:
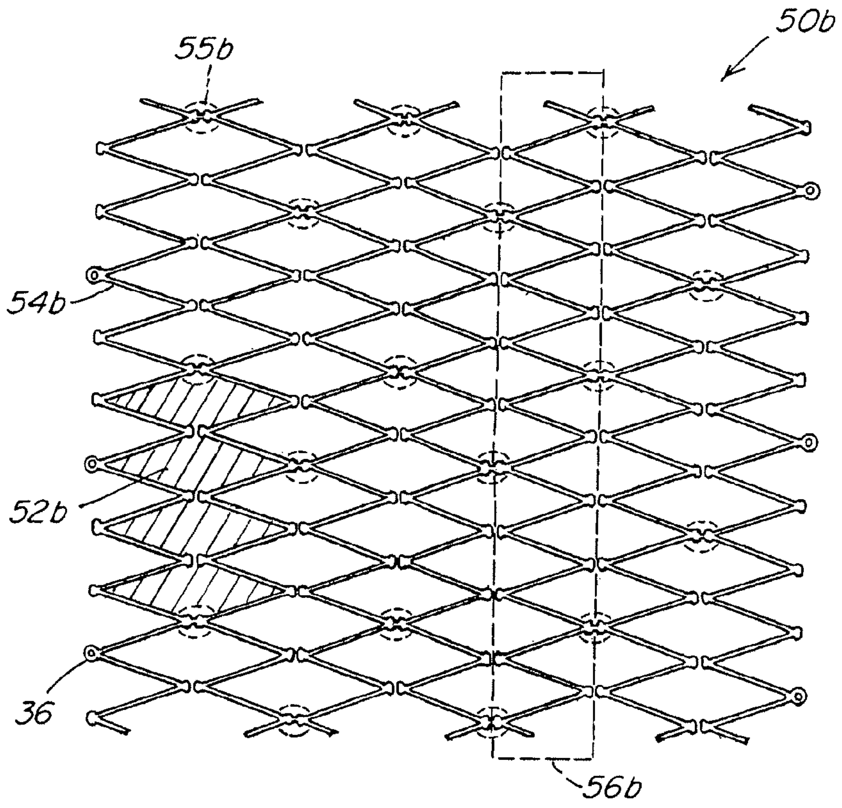
Figure 5C:
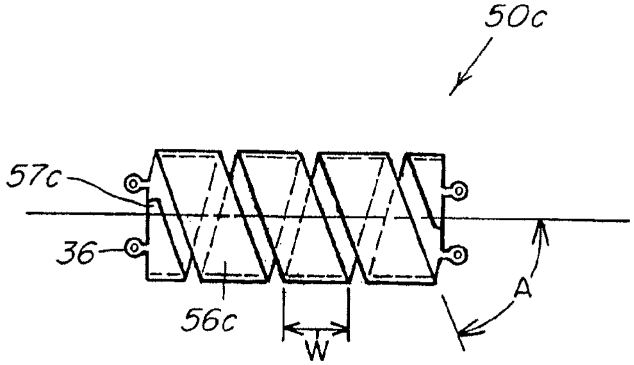
FIG. 5C illustrates side views of exemplar medical device embodiments having features in accordance with the principles of the present disclosure.

FIG. 5A illustrates stent 50*a* comprised of cells 52*a*, struts 54*a*, and radiopaque marker interlocks 36. Stent cells 52*a* are connected to adjacent cells 52*a* by means of interconnection regions 55*a*. FIG. 5B illustrates fracturable stent 50*b* comprised of cells 52*b*, struts 54*b*, and radiopaque marker interlocks 36. Stent cells 52*b* are connected to adjacent cells 52*b* by means of fracturable interconnection regions 55*b*. Fracturable interconnection regions 55*b* are designed to fracture over time so as to improve fatigue life of stent 50*b*. Deployed stent integrity after fracture of interconnection regions 55*b* is maintained because rows 56*b* of struts 54*b* in a zig-zag pattern form structurally intact rings in deployed stent. FIG. 5C illustrates coil stent 50*c* comprised of ribbon or wire 56*c* and radiopaque marker interlocks 36. Ribbon or wire 56*c* has width W and is wound into a hollow cylinder form having a wind angle A. Ends 57*c* of ribbon may be rounded to prevent tissue damage or tissue irritation in vicinity of ends 57*c* when stent 50*c* is implanted into a patient. In one embodiment ribbon 56*c* is comprised of cells and struts arranged in an expandable architecture (not shown) having similarity to the cellular structures described in connection with at least FIGS. 5A and 5B.

Improved inner member 14, interlock assembly(ies), and outer member cooperate to place the implant in tension during deployment, thereby reducing implant deployment force. With reference to FIGS. 1-3, when sheath 16 is retracted implant 12 will attempt to retract with sheath 16 due to the frictional forces of the self expanding implant against inner diameter of sheath. However, enlarged ends 36 of implant 12, engaged with distal interlock structure 29 will prevent implant 12 from retracting proximally because interlock structure 29 is attached to inner member 14. Column strength of improved inner member 14 will resist compression and thereby place implant 12 in tension when sheath 16 is retracted. When implant 12 is in tension it will elongate slightly with a commensurate slight reduction in diameter, thereby reducing the frictional forces of the self expanding implant against inner diameter of sheath and the deployment force needed to move handles 37, 39 during sheath retraction and associated implant deployment. The frictional reduction described will occur until enlarged ends 36 have expanded sufficiently to disengage from distal interlock structure 29. Thereafter mid interlock structures 28, if used, will similarly resist retraction of implant 12 during retraction of sheath 16 and will lessen implant deployment forces. In one embodiment, a 150 mm stent deployed from a stent delivery system having mid or distal interlocks has a deployment force of 50 to 600 grams. In another embodiment, a 150 mm stent deployed from a stent delivery system having mid or distal interlocks has a deployment force of 100 to 400 grams. In another embodiment, a 150 mm stent deployed from a stent delivery system having mid or distal interlocks has a deployment force of 150 to 300 grams. In an alternate embodiment, a 200 mm stent deployed from a stent delivery system having mid or distal interlocks has a deployment force of 50 to 600 grams. In another embodiment, a 200 mm stent deployed from a stent delivery system having mid or distal interlocks has a deployment force of 100 to 400 grams. In another embodiment, a 200 mm stent deployed from a stent delivery system having mid or distal interlocks has a deployment force of 150 to 300 grams.

In another embodiment, distance between distal interlock structure 29 and proximal interlock structure 27 is longer than distance between distal end 12*b* of stent 12 and proximal end 12*a* of stent 12 in order to preload stent 12 into the delivery system under tension. In this embodiment column strength of improved inner member 14 resists axial compressive creep of inner member so that preloaded stent tension is maintained under storage, sterilization, and shipping conditions. Stents preloaded in tension to lengths 1% greater than their length under no tension within sheath 16, 66 ("1% preloaded tension") to lengths 15% greater than their length under no tension within sheath 16, 66 ("15% preloaded tension") are contemplated. In one embodiment, stents are preloaded with 2% preloaded tension. In another embodiment, stents are preloaded with 3% preloaded tension. In another embodiment, stents are preloaded with 5% preloaded tension. In another embodiment, stents are preloaded with 8% preloaded tension. In another embodiment, stents are preloaded with 12% preloaded tension.

Figure 6A:
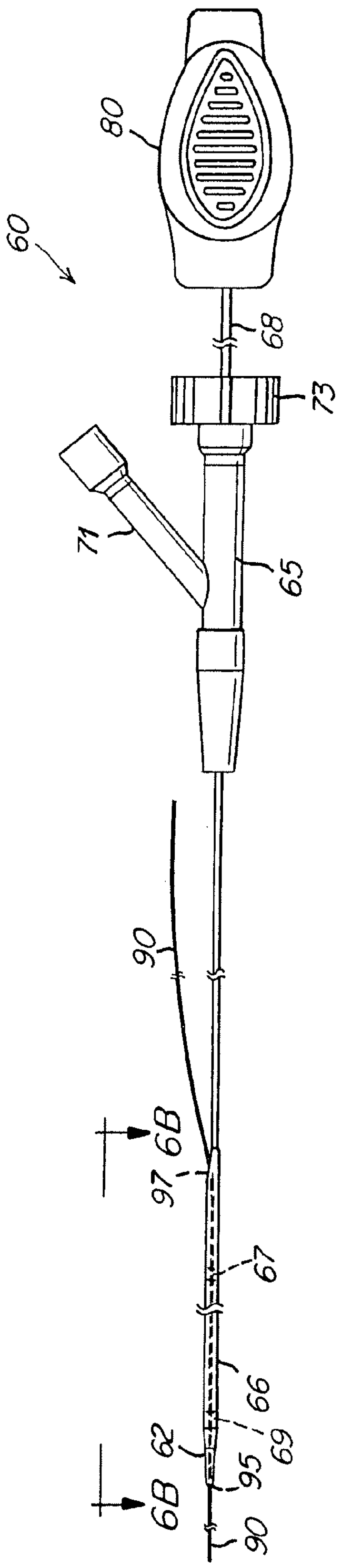
FIGS. 6A and 6B are side elevation views of an alternate embodiment of an implant delivery system having features that are examples of inventive aspects in accordance with the principles of the present disclosure.
Figure 6B:
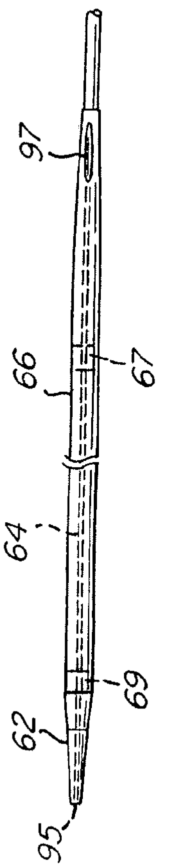

FIGS. 6A and 6B illustrate an alternate embodiment of a medical device delivery system. Rapid exchange stent delivery system 60 includes sheath 66 and inner member 64 disposed within sheath. Manifold housing 65 is coupled to sheath 66. Housing 71 includes side arm 71 and locking member 73. Push wire 68 is coupled to inner member 64 at its distal end and to handle 80 at its proximal end. Inner member 64 and sheath 66 are axially slideable relative to one another. Push wire 68 and housing 65 are used to facilitate movement of inner member 64 relative to sheath 66. Locking member 73 can be operated to couple housing 65 to push wire 68 in order to slide both sections along together. Relative movement between the inner member and the sheath is permitted to define a transport position and a deploy position of the system 60. Stent (not shown) mounts over inner member 64 and is covered by sheath 66 so as to be retained in the collapsed state. The stent is released (i.e., deployed) by retracting sheath 66 to uncover or expose stent. System 60 includes proximal interlock structure 67 that prevents stent from prematurely deploying, one or more mid interlock structure (not shown) that assist with uniform stent deployment and with stent loading, and one or more distal interlock structure 69 that assist with uniform stent deployment and with stent loading. Upon release of the stent from stent delivery system 60, the stent expands to an enlarged diameter to abut against the walls of the patients lumen in order to support patency of the lumen. The expansion of the stent also causes stent to disengage from proximal, mid, and distal interlock structures.

Sheath 66 may be made of kink resistant extruded polymer tubing with adequate strength and lubricity for unsheathing a stent. Polymers such as nylon, PEBAX, polyethylene, or polyester may be used. Alternatively, thermoset polymers such as polyimide or braid reinforced polyimide may be used. In some embodiments the distal portion of the outer member is transparent to allow inspection of the stent within. Inner member 64 is comprised of one or more materials having good flexibility when bent transverse to inner member central axis and high stiffness when compressed along inner member central axis. Inner member 64 is comprised of materials described in connection with the examples illustrated in FIGS. 4A-4G. Push wire 68 in one embodiment is constructed of metal. In one embodiment the proximal portion of push wire is comprised of stainless steel tubing and the distal portion of push wire 68 is comprised of metal wire. This combination provides adequate column strength throughout, good bending resistance proximally, and good bending flexibility distally. Housing 65 and locking member 73 may be comprised of polycarbonate, polystyrene, or other materials, and a sealing gland (not shown) may be used in cooperation with housing 65 and locking member 73 to effect a fluid seal and/or mechanical lock between housing, locking member, and push wire 68 as is well known in the art. Handle 80 may be comprised of polycarbonate, polystyrene, nylon, or other materials. Alternate materials for these components are generally well known in the art and can be substituted for any of the non-limiting examples listed above provided the functional requirements of the component are met.

Guidewire 90 has a nominal outer diameter of 0.010"-0.038". In one embodiment guidewire 90 has a nominal outer diameter of 0.014". Inner member 64 and tip 62 are dimensioned to allow low friction passage of guidewire 90 within guide wire lumen 95 and through RX port 97. Guide wire lumen length can vary widely, but ranges in length from 5 cm to 50 cm are contemplated. In one embodiment guide wire lumen 95 is approximately 30 cm in length. Sheath maximum outside diameter can range from about 10 Fr to about 3 Fr. A sheath outside diameter of about 5 Fr is desirable for compatibility with currently popular guide catheter (not shown) dimensions. Sheath length can be varied to suit the application of interest. Sheath lengths of 40 cm-200 cm are contemplated. In one embodiment sheath length is about 145 cm.

An exemplar method of using a medical device delivery system having improved inner member in a body of a patient is now described. Using techniques well known in the art, a guidewire is percutaneously inserted into a patient's blood vessel and advanced to a region of interest in the patient's body. Using imaging techniques such as fluoroscopy a diseased portion of the vessel is identified and a stent having the correct length and diameter for treating the diseased portion is chosen. With reference to FIGS. 1, 2, 3, 6A and 6B, self expanding medical device delivery system 10, 60 loaded with stent 12 is advanced over the guidewire to the treatment site and by using imaging techniques such as fluoroscopy stent 12 is positioned at a correct location relative to the treatment site.

Inner member 14, 64 is held stationary and sheath 16, 66 is withdrawn to expose stent 12. Stent 12 expands into contact with a lumenal wall of the vessel as sheath 16, 66 is withdrawn. Distal interlock 29, 69 in combination with column stiffness of improved inner member 14, 64 causes stent to axially elongate when sheath 16, 66 is withdrawn, thereby reducing forces required to withdraw sheath 16, 66. Mid interlocks 28 (if used) in combination with column stiffness of improved inner member 14, 64 cause stent to axially elongate when sheath 16, 66 is withdrawn thereby reducing forces required to withdraw sheath 16, 66. Proximal interlocks 27, 67 secure stent to stent delivery catheter until sheath 16, 66 is withdrawn proximally of stent end 12*a*, thereby facilitating deployment of proximal end 12*a* of expanded stent at the correct location. After, and optionally, during stent deployment, stent markers 15 are imaged for various reasons including evaluating deployed stent position relative to treatment site, evaluating extent of stent diametrical expansion, and other reasons.

Figure 7A:
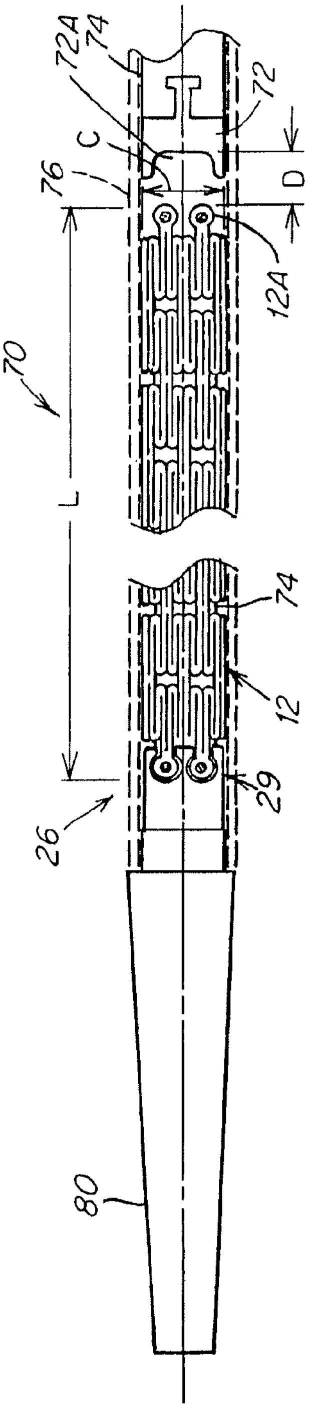
FIGS. 7A, 7B and 7C are side elevation views of an alternate embodiment of an implant delivery system having features that are examples of inventive aspects in accordance with the principles of the present disclosure.
Figure 7C:
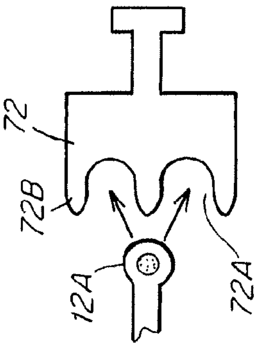
Figure 7B:
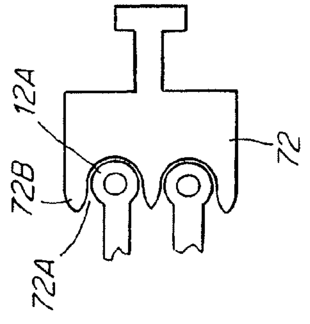

FIGS. 7A, 7B and 7C show an alternate embodiment of a distal portion 70 of over the wire stent delivery system 10 or rapid exchange stent delivery system 60. Distal portion 70 is comprised of distal tip 80, distal retainer 29, self-expanding stent 12, inner member 74, sheath 76, and proximal pusher 72. The function of and materials of construction of distal tip 80, distal retainer 29, self-expanding stent 12, inner member 74, and sheath 76 are substantially similar to the function of and materials of construction of distal tips 30 & 62, distal retainers 29 & 69, self-expanding stent 12, inner members 14 & 64, and sheaths 16 & 66 described earlier for delivery systems 10 & 60. In one embodiment proximal pusher 72 is fixedly attached to inner member 14 adjacent stent mounting location 26. For example, proximal pusher 72 can be bonded, crimped, swaged, affixed, fastened, fused, molded in, embedded in, or otherwise secured to inner member 14. Some embodiments include a proximal pusher formed as an integral/unitary structure with the inner member. In other embodiments, a proximal pusher in the form of a separate piece can be secured to inner member 14. For example, a proximal pusher can be machined, etched, stamped, formed, or otherwise fabricated into the surface of a ring of metal, engineering polymer, ceramic, or other material and the ring applied to the inner member by adhesive bonding, welding, solvent welding, fusing, or other techniques known in the art.

Proximal pusher 72 is comprised of channels 72A sized to slideably receive one or more stent end 12A. FIG. 7A illustrates two stent ends 12A positioned at a distance distal to proximal pusher 72 and FIG. 7B illustrates one stent end 12A positioned within each channel 72A of proximal pusher 72. Proximal pusher 72 is further comprised of deflecting ends 72B configured to deflect stent ends 12A into channel 72A. In one embodiment deflecting ends 72B have a shape similar to that of the leading portion of a bullet. In other embodiments deflecting ends 72B have round, ovoid, pointed, tapered, or other shapes that will deflect stent ends away from deflecting ends 72B (in direction of either arrow in FIG. 7C) and into channels 72A.

As illustrated in FIG. 7A, there is a gap D between proximal pusher 72 and proximal-most end 12*a* of stent 12. Gaps D ranging from 1 mm to 15 mm are contemplated. In one embodiment gap D is 3 mm long. In another embodiment gap D is 5 mm long. In another embodiment gap D is 8 mm long. In another embodiment gap D is 12 mm long.

Stent delivery systems have been manufactured according to the principles of the invention and have been found to have superior stent deployment forces as shown in the examples below.

Example 1

Stents 6 mm in diameter and 150 mm or 200 mm long and having structures similar to that shown in FIG. 5A were laser cut from binary nitinol alloy tubing, expanded, and heat treated using processes known in the art. Stents (150 mm long or 200 mm long) were mounted on prior art Stent Delivery Systems (SDS) and stents (200 mm long) were mounted on inventive SDS. Aside from differences associated with stent length, inventive SDS were identical to prior art SDS except that 1) distal interlocks were present on inventive SDS and absent on prior art SDS, and 2) inventive SDS were comprised of proximal pushers while prior art SDS were comprised of proximal retainers, and 3) inventive SDS were comprised of improved inner members while prior art SDS were comprised of prior art inner members. Improved inner members (0.380" inside diameter×0.045" outside diameter) were comprised of 0.001" thick polyimide inner layer, 0.0015" thick nylon 12 outer layer and 16 braided type 304V stainless steel reinforcing strands of 0.0005"×0.0030" flat wire. All 3 layers were heat bonded to each other. Prior art inner members of the same overall dimensions were comprised of non-reinforced nylon 12. Both stent delivery systems were tested for maximum stent deployment force under similar testing conditions.

As the table below shows, the inventive SDS has superior measured characteristics as compared to the prior art SDS. For 6 mm×200 mm stents both the average deployment force and the variability of deployment force were reduced due to the inventive design. In addition, 6 of 21 6 mm×200 mm stents were unable to be deployed in the prior art SDS because the SDS fractured under excessively high deployment forces. Further, 6 mm×150 mm stents in prior art SDS had similar deployment forces as longer stents (6 mm×200 mm) in inventive SDS. This is particularly significant because longer stents have been shown to require higher deployment forces than shorter stents in a given SDS.

| Stent Size: Diameter × Length (mm) | Inventive SDS Deployment Force (lbs) | Prior Art SDS Deployment Force (lbs) |
|---|---|---|
| 6 × 150 | — | 1.41 ± 0.15 |
| 6 × 200 | 1.38 ± 0.12 | 1.72 ± 0.40* |

*unable to deploy 6 of 21 units due to fracture of SDS

An exemplary method of using a medical device delivery system having improved inner member and alternate embodiment of a distal portion 70 in a body of a patient is now described. Using techniques known in the art, a guidewire is percutaneously inserted into a patient's blood vessel and advanced to a region of interest in the patient's body. Using imaging techniques such as fluoroscopy a diseased portion of the vessel is identified and a stent having the correct length and diameter for treating the diseased portion is chosen. With reference to FIGS. 1, 2, 3, 6A, 6B, 7A and 7B self expanding medical device delivery system 10, 60 having distal portion 70 and loaded with stent 12 is advanced over the guidewire to the treatment site and by using imaging techniques such as fluoroscopy stent 12 is positioned at a correct location relative to the treatment site.

Inner member 14, 64 is held stationary and sheath 16, 66 is withdrawn to expose stent 12. Due to friction, self expanding stent 12 will move proximally with sheath 16, 66 but distal retainer in cooperation with distal ends of stent and improved inner member 14, 64 will prevent stent distal ends from moving proximally. Because of this, stent 12 will lengthen and reduce gap D, thus reducing its constrained diameter, reducing the frictional force of the stent against the inside diameter of the sheath, and thereby reducing the force needed for initial stent deployment. The sheath will retract relative to the distal end of the stent a small amount, allowing the distal ends of the stent to radially expand and thereby free themselves from the distal retainer 29. Once the stent distal ends are free, the stent will move proximally with the sheath 16, 66, further reducing gap D, until the stent proximal ends bottom out in channels 72A of proximal pusher 27 and gap D is reduced to zero. At this point continued withdrawal of sheath will cause proximal pusher 72 to push stent 12 out of sheath 16, 66. Stent 12 expands into contact with a lumenal wall of the vessel as sheath 16, 66 is withdrawn.

After, and optionally, during stent deployment, stent markers 15 are imaged for various reasons including evaluating deployed stent position relative to treatment site, evaluating extent of stent diametrical expansion, and other reasons.

Alternative Interlock Embodiments

Stent 12 has a deployed length L and a circumference C, and includes a plurality of struts 86 (i.e., reinforcing members). At least some of the struts 86 have free terminal ends 40 that define proximal and distal ends 12*a* and 12*b* of the stent 12. The stent 12 includes an interlock geometry in the form of enlargements 36, 47 positioned at the free terminal ends of the struts 86. As shown in FIG. 3, the enlargements are circular enlargements. It will be appreciated that other shapes and interlock configurations could also be used. The enlargements 36, 47 project outwardly from the struts 86 in a circumferential direction (i.e. in a direction coinciding with the circumference C of the stent 12). In one embodiment, the stent 12 can be manufactured by cutting (e.g., laser cutting) the various features from a solid tube of material. When manufactured by this technique, the enlargements 36, 47 do not project radially beyond an inner and outer diameter of the stent.

Stent interlock structures 27, 28 and 29 may be comprised of enlarged stent ends (designated generically as 12*x* in FIGS. 8A through 8N) and retainers (designated-generically as cavities 14*y* or pin 14*z* in the Figures) and are located adjacent stent mounting location 26 of stent delivery system 10. Stent interlock structures 27, 28 and 29 comprised of retainers 14*y*, 14*z* and may be are preferably fixedly attached to inner member 14 adjacent mounting location 26. For example, stent interlock structures 27, 28 and 29 can be bonded, crimped, swaged, affixed, fastened, fused, molded in, embedded in, or otherwise secured to inner member 14. In an alternate embodiment, stent interlock structures 27, 28 and 29 may be comprised of stent ends having cavities and retainers comprised of interlocking enlarged ends and are located adjacent stent mounting location 26 of stent delivery system 10.

Figure 8A:
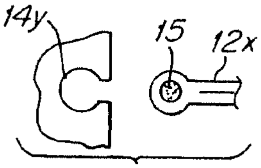
FIGS. 8A to 8N illustrate plan views of stent delivery system interlock structures. The stent and the retainer are shown cut longitudinally and laid flat with an axial separation between the stent end and the mating retainer structure.
Figure 8B:
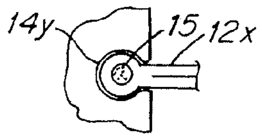
Figure 8C:
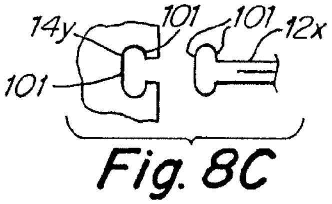
Figure 8D:
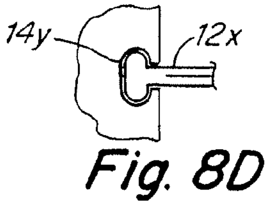
Figure 8E:
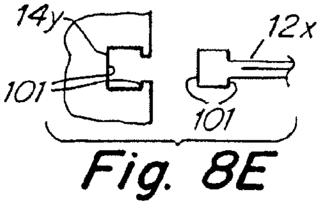
Figure 8F:
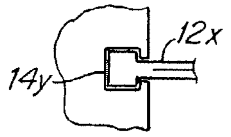
Figure 8G:
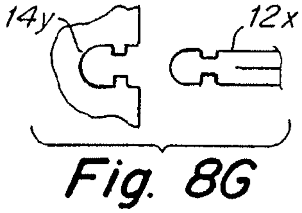
Figure 8H:
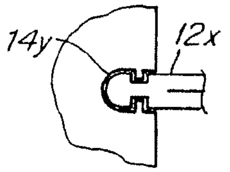
Figure 8I:
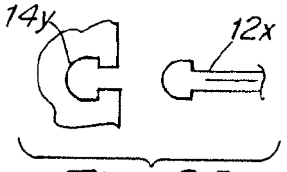
Figure 8J:
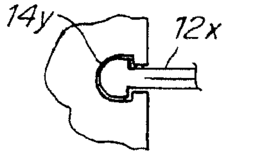
Figure 8K:
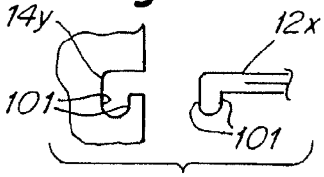
Figure 8L:
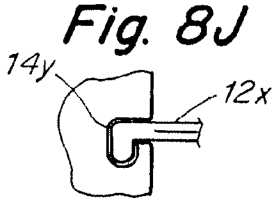
Figure 8M:
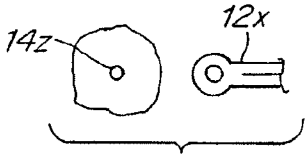
Figure 8N:
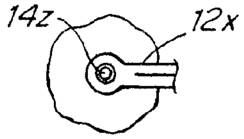

FIGS. 8A through 8N illustrate 7 different exemplary interlock configurations. In one embodiment one or more of the interlock configurations illustrated in FIGS. 8A through 8N are applied to either proximal end 12*a* or distal end 12*b* of stent 12 and to corresponding locations of inner member 14. In some embodiments one or more of the interlock configurations illustrated in FIGS. 8A through 8N are applied to stent 12 in between proximal end 12*a* and distal end 12*b* of stent 12. In all of the FIGS. 8A through 8N, stent ends 12*x* are shown in relation to corresponding retainers 14*y*, 14*z*. In each of the paired Figures (i.e. FIGS. 8A-8B, 8C-8D, 8E-8F, 8G-8H, 8I-8J, 8K-8L and 8M-8N), the stent end and the retainer have been cut longitudinally and laid flat. In the first Figure of each pair (e.g. FIG. 8A), the retainer 14*y* or 14*z* and the stent end 12*x* are shown disengaged from one another. In the second Figure of each pair (e.g. FIG. 8B), the retainer and the stent end are shown interlocked.

The interlock configurations illustrated in FIGS. 8A through 8N are comprised of opposing surfaces 101 that mechanically interfere with proximal or distal movement of stent ends 12*x* relative to retainers 14*y*, 14*z* along the lengthwise axis of stent but which allow radial movement of the stent ends 12*x* out of the retainers 14*y*, 14*z*. In an alternate embodiment (not shown) stent 12 is comprised of retainers as part of stent ends 12*x* and inner member 14 is comprised of corresponding interlock geometry.

In an alternate embodiment, stent ends 12*x* are comprised of one or more imagable markers 15 as illustrated in FIGS. 8A and 8B. In the illustrated embodiment, stent 12 includes radiopaque markers 15 that permit a physician to accurately determine the position of stent 12 within the patient's lumen under fluoroscopic visualization. In another embodiment, stent 12 includes ultrasonic markers 15 that permit a physician to accurately determine the position of stent 12 within the patient's lumen under ultrasonic visualization. In a further embodiment, stent 12 includes MRI safe markers 15 that permit a physician to accurately determine the position of stent 12 within the patients lumen under magnetic resonance imaging. Ultrasonic and MRI visualization are especially useful for visualizing stent 12 during non-invasive follow-up and monitoring. Markers 15 may be are preferably located adjacent the proximal or distal ends 12*a*, 12*b* of stent 12 or both and may be located along the length of the stent between the proximal and distal stent ends 12_a_, 12_b_. Markers 15 can be attached to stent 12 by techniques such as adhesive, beat fusion, interference fit, fasteners, intermediate members or other techniques. Materials for making radiopaque marker 15 should have a density suitable for visualization through fluoroscopic techniques. Preferably, the markers may have a radiopacity substantially greater than the material forming the struts of the stent. Exemplary materials comprise tantalum, platinum, gold, tungsten and alloys of such metals. In some embodiments, the markers can be coated with a radiopaque material or filled with radiopaque material. Materials for making ultrasonic marker 15 should have an acoustical density sufficiently different from stent 12 to provide suitable visualization through ultrasonic techniques. Exemplary materials comprise polymers (for metallic stents), metals such as tantalum, platinum, gold, tungsten and alloys of such metals (for polymeric or ceramic stents), hollow glass spheres or microspheres, and other materials. Materials for making MRI safe marker 15 should be non-ferrous and have a magnetic signature sufficiently different from stent 12 to provide suitable visualization through MRI techniques. Exemplary materials comprise polymers (for metallic stents), metals such as tantalum, platinum, gold, tungsten and alloys of such metals (for polymeric or ceramic stents), and other materials.

In the illustrated embodiments shown in FIGS. 2-8B, markers 15 are at least partially defined at the interlock geometries located at the ends of stent 12. In one embodiment, enlargements 47 may define openings in the form of through-holes or through-apertures (i.e., holes that extend completely through the enlargements 47) within which markers 15 may be positioned. For example, markers in the form of insert pieces can be press-fit or riveted within the through-holes. In another embodiment, the enlargements may include openings in the form of recesses (depressions that extend partially through the enlargements) within which marker 15 may be placed. Positioning markers 15 on ends 12_a_, 12_b_ of stent 12 provides precise stent location information to a physician, even after deployment and removal of the stent delivery device.

Some of the embodiments depicted herein include stent-retaining structures having interlocks formed as an integral/unitary structure with the inner member. In alternate embodiments stent retainers in the form of separate pieces can be secured to inner member 14. For example, retainers 14_y_, 14_z_ can be machined, etched, stamped, formed, or otherwise fabricated into the surface of a ring of metal, engineering polymer, ceramic, or other material and the ring applied to inner member 14-19 by adhesive bonding, welding, solvent welding, fusing, or other techniques known in the art.

Figure 9:
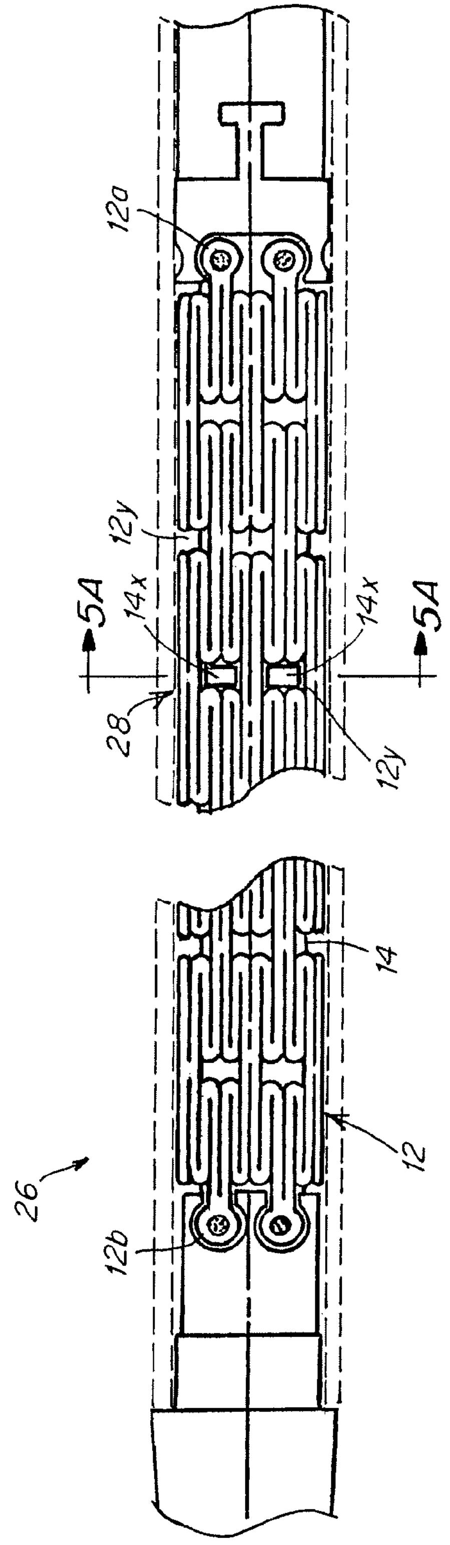
FIG. 9 is an enlarged view of the distal end of an embodiment of a stent delivery system having inventive aspects in accordance with the principles of the present disclosure with an outer sheath shown in phantom line.
Figure 9A:
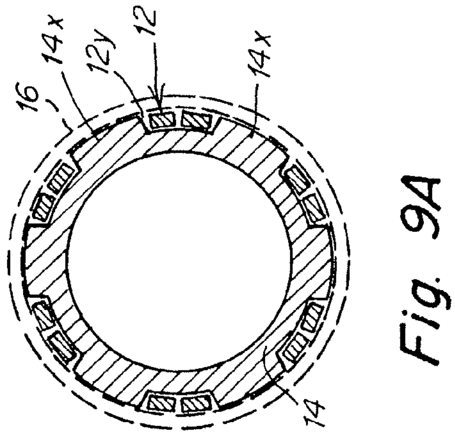
FIG. 9A is a cross section of a portion of the stent system illustrated in FIG. 5.

FIGS. 9 and 9A illustrate an alternative embodiment of stent mid interlock geometry 28. Stent 12 is comprised of retainers 12_y_ in the form of pockets or voids in the compressed stent structure. One or more protrusion 14_x_ emanate from inner member 14 and in another embodiment are integral to and fixedly attached to inner member 14 adjacent mounting location 26. For example, protrusion 14_x_ can be bonded, crimped, swaged, affixed, fastened, fused, molded in, embedded in, raised from or otherwise secured to inner member 14. In some embodiments mid interlock geometry 28 is applied to stent 12 and inner member 14 in between proximal end 12_a_ and distal end 12_b_ of stent 12 at one or more locations along the length of the stent. FIGS. 9 and 9A illustrate retainers 12_y_ and protrusions 14_x_ in an interlocked configuration.

In various embodiments, Mid-interlocks are particularly useful for stents ranging from between any of 100 mm to 500 mm in length, more preferably ranging from 150 to 300 mm in length, or and more preferably ranging even from 150 to 200 mm in length.

Figure 10:
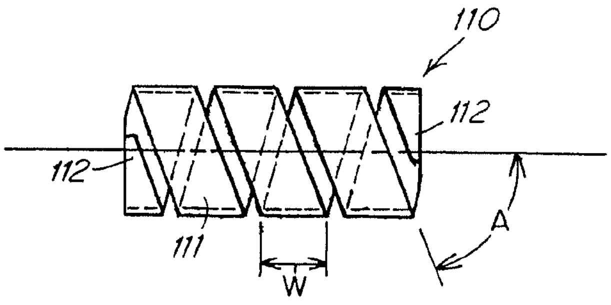
FIGS. 10 and 11 illustrate side views of an exemplar stent embodiment having structure that interlocks with structure of a delivery catheter, the stent is shown expanded.
Figure 11:
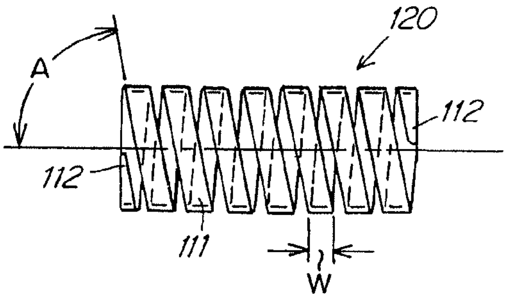

FIGS. 10 and 11 illustrate stent embodiments having structures that interlock with structure of a delivery catheter. Coil stents 110, 120 are comprised of ribbon 111 having width W, wound into a hollow cylinder form and having a wind angle A. Stent 120 is comprised of ribbon 111 having width W less than width of ribbon in stent 110, and having wind angle A greater than wind angle A of ribbon in stent 110. Ends 112 of ribbon may be rounded to prevent tissue damage or tissue irritation in vicinity of ends 112 when stent 110, 120 is implanted into a patient. Ribbon 111 may be comprised of metal, polymer, ceramic, permanent enduring materials, or bioabsorbable materials. Bioabsorbable ribbons 111 can be polymeric, bio-polymeric, ceramic, bio-ceramic, or metallic, or may be made from combinations of these materials. Bioabsorbable and non-bioabsorbable ribbons 111 may elute over time substances such as drugs. The stencil stranded in FIGS. 10 and 11 may be modified to include any of the interlock configurations described herein, one of which is illustrated in FIG. 5C. It is contemplated that the interlock geometries and configurations described herein may be implemented with various stent types and designs, in addition to those disclosed herein, for example with those published in International Application PCT/US 06/015596, Publication Number W0 2006/116383, the subject matter of which is incorporated herein by reference.

Figure 12:
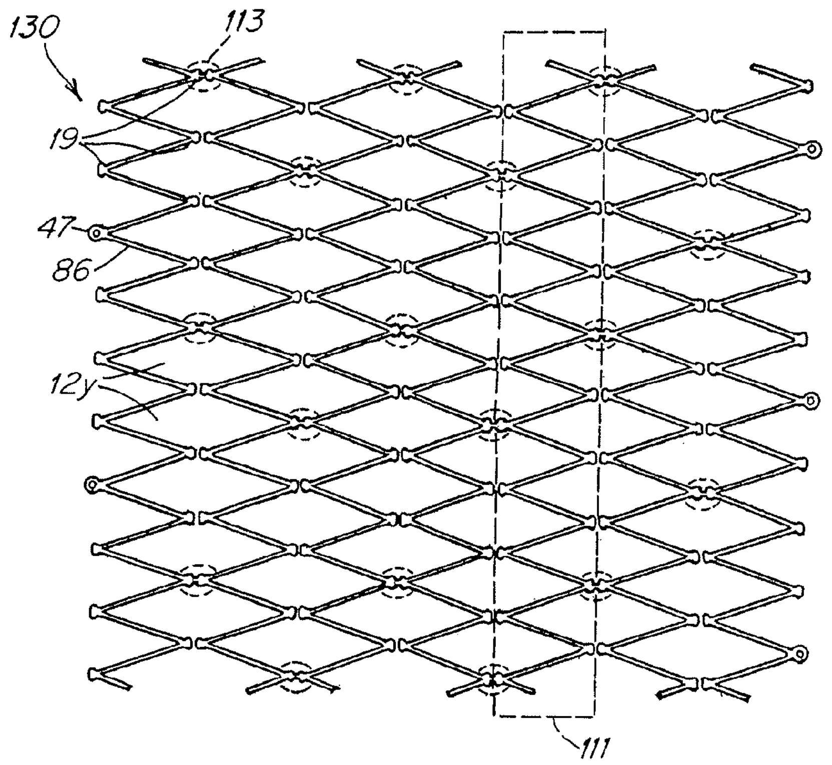
FIG. 12 illustrates a plan view of an exemplar stent embodiment having structure that interlocks with structure of a delivery catheter, the stent is shown expanded and the stent and interlock structures are shown cut longitudinally and laid flat.

Ribbon 111 is comprised of an expandable architecture 130. One example of an expandable architecture 130 is illustrated in FIG. 12. Ribbon 111 is shown partially expanded and the ribbon and interlock structures are shown cut longitudinally and laid flat. Expandable architecture 130 is comprised of enlarged ends 47, mid-stent retainer pockets 12_y_, struts 86, bend regions 19, and one or more interconnection regions 113. Struts 86 and bend regions 19 together form a zig-zag shaped expandable architecture of ribbon 111. Other expandable architectures are contemplated for expandable architecture of ribbon 111 such as various serpentine or meandering paths. Interconnection regions 113 join adjacent ribbons 111 and can fracture in a controlled manner such that when fractured interconnection regions 113 no longer join adjacent ribbons 111.

Figure 13:
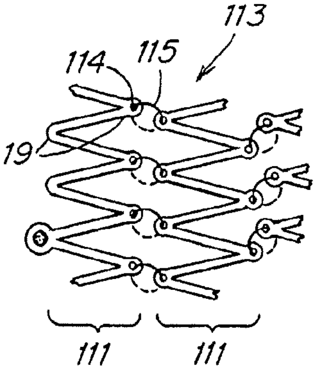
FIGS. 13 and 14 illustrate plan views of a section of an exemplar stent embodiment having structure that interlocks with structure of a delivery catheter, the stent is shown partially expanded and the stent segment and interlock structures are shown cut longitudinally and laid flat.

In one embodiment, illustrated in FIG. 13, interconnection regions 113 are comprised holes 114 in bend regions 19 and one or more strand 115. Strand 115 passes through holes 114 along a pathway that joins together adjacent ribbons 111. In the example illustrated in FIG. 20, strand 115 passes through holes 114 in adjacent bend regions 19 and forms a closed loop. Many other strand pathways are possible, such as a single strand 115 passing through holes 114 of multiple bend regions 19, and other configurations as are apparent to those skilled in the art. Strand 115 is comprised of a material that fractures in a controlled manner, and may be formed of biodegradable suture or other materials. In an alternate embodiment interconnection regions 113 are comprised of a biodegradable coupling such as a tube that surrounds bend regions 19. In another alternate embodiment, interconnection regions 113 are comprised of a biodegradable rivet that passes through holes 114 in adjacent bend regions 19.

Figure 14:
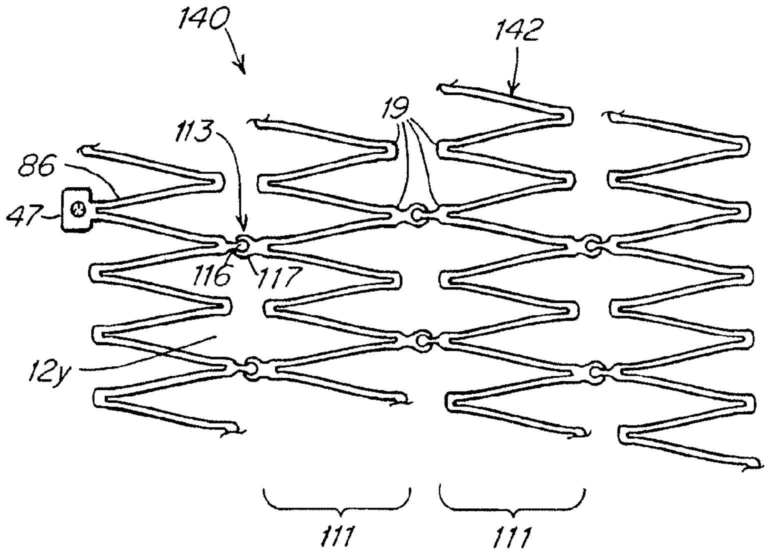

FIG. 14 illustrates stent 140 having interlock structures that interlock with interlock geometry of a delivery catheter, comprised of ribbon 111 having expandable architecture 142. Expandable architecture 142 is comprised of enlarged ends 47, mid-stent retainer pockets 12_y_, struts 86, bend regions 19, and one or more interconnection regions 113. Struts 86 and bend regions 19 together form a zig-zag shaped expandable architecture of ribbon 111. Other expandable architectures are contemplated for expandable architecture of ribbon 111 such as various serpentine or meandering paths. Interconnection regions 113 join adjacent ribbons 111 and can fracture in a controlled manner such that when fractured, interconnection regions 113 no longer join adjacent ribbons 111.

Interconnection regions 113 are comprised of expanded ends 116 and receiver ends 117 in bend regions 19. Expanded ends 116 and receiver ends 117 join together adjacent ribbons 111, preventing axial separation of adjacent ribbons when stent 140 is contracted or expanded. Expanded ends 116 and receiver ends 117 may translate relative to one another in a radial direction relative to the stent longitudinal axis such that adjacent ribbons 111 are no longer joined together. Many other expanded end/receiver end geometries beyond that illustrated are possible provided the functional requirements of ends 116, 117 are met, as will be apparent to those skilled in the art.

Figure 15:
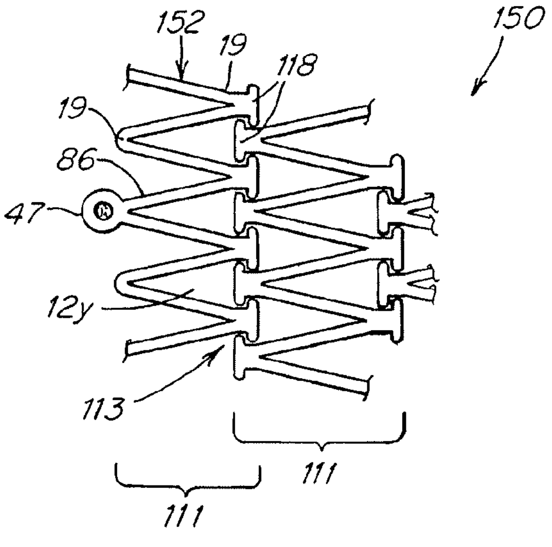
FIG. 15 illustrates plan views of a section of an exemplar stent embodiment having structure that interlocks with structure of a delivery catheter, the stent is shown contracted and the stent segment and interlock structures are shown cut longitudinally and laid flat.

FIG. 15 illustrates stent 150 having interlock structure that interlocks with interlock geometry of a delivery catheter, comprised of ribbon 111 having expandable architecture 152. Expandable architecture 152 is comprised of enlarged ends 47, mid-stent retainer pockets 12*y*, struts 86, bend regions 19, and one or more interconnection regions 113. Struts 86 and bend regions 19 together form a zig-zag shaped expandable architecture of ribbon 111. Other expandable architectures are contemplated for expandable architecture of ribbon 111 such as various serpentine or meandering paths. Interconnection regions 113 join adjacent ribbons 111 and can fracture in a controlled manner such that when fractured, interconnection regions 113 no longer join adjacent ribbons 111.

Interconnection regions 113 are comprised interdigitating ends 118 in bend regions 19. Interdigitating ends 118 join together adjacent ribbons 111 by mechanical interference against each other when stent 150 is contracted. Upon expansion of stent 150 interdigitating ends 118 become separated along circumference of stent 150 such that adjacent ribbons 111 are no longer joined together. Many other interdigitating end geometries beyond that illustrated are possible provided the functional requirements of ends 118 are met, as will be apparent to those skilled in the art.

Figure 16:
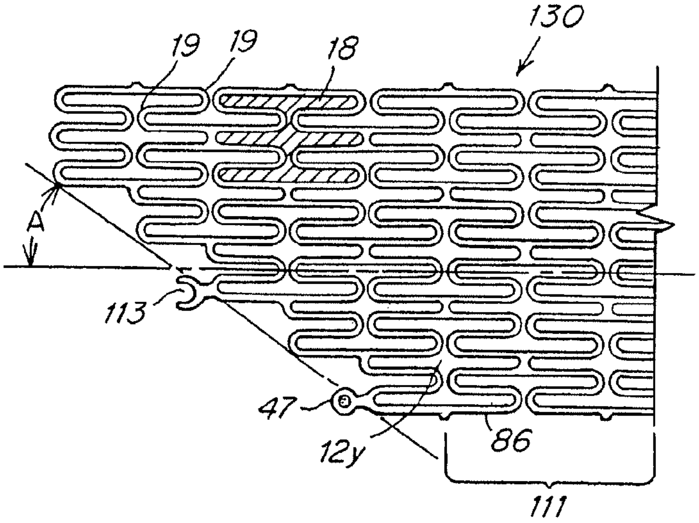
FIG. 16 illustrates a plan view of a section of an exemplar stent embodiment having structure that interlocks with structure of a delivery catheter, the stent is shown partially expanded and the stent segment and interlock structures are shown cut longitudinally and laid flat.

FIG. 16 illustrates another example of an expandable architecture 130. A fractional portion of ribbon 111 is shown partially expanded and the ribbon and interlock structures are shown cut longitudinally and laid flat. Expandable architecture 130 is comprised of cells 18, enlarged ends 47, mid-stent retainer pockets 12*y*, struts 86, bend regions 19, and one or more interconnection regions 113. Struts 86 and bend regions 19 together form a cellular expandable architecture of ribbon 111 with similarities to the cellular structures described in connection with at least FIGS. 2, 3, 5, 7, 8, 10, 11 and 12. Interconnection regions 113 join adjacent ribbons 111 and can fracture in a controlled manner such that when fractured, interconnection regions 113 no longer join adjacent ribbons 111. Interconnection regions 113 may be comprised of expanded ends 116 and receiver ends 117, interdigitating ends 118, or other structures.

The invention contemplated is suitable for stents in addition to those cited herein. For example, stents having interlock structure that interlocks with interlock geometry of a delivery catheter may be comprised tapered stents, flared stents, braided stents, bifurcation stents, and other stents as are known in the art. Tapered stents generally have a proximal end of one diameter and a distal end of a second diameter (typically a smaller diameter). Flared stents generally have a short tapered portion at the proximal end of a cylindrical stent, where the flared section is larger in diameter than the cylindrical portion. Braided stents are typically comprised of a tube manufactured by using a braiding method. An example of a braided stent is the Wallstent, sold by Boston Scientific, Natick, Mass. Bifurcation stents are placed in a patient where a vessel branches. Bifurcation stents are generally comprised of a single stent portion that branches into two stent portions and appears similar to a Y-fitting used to connect one piece of tubing to two pieces of tubing.

Figure 17:
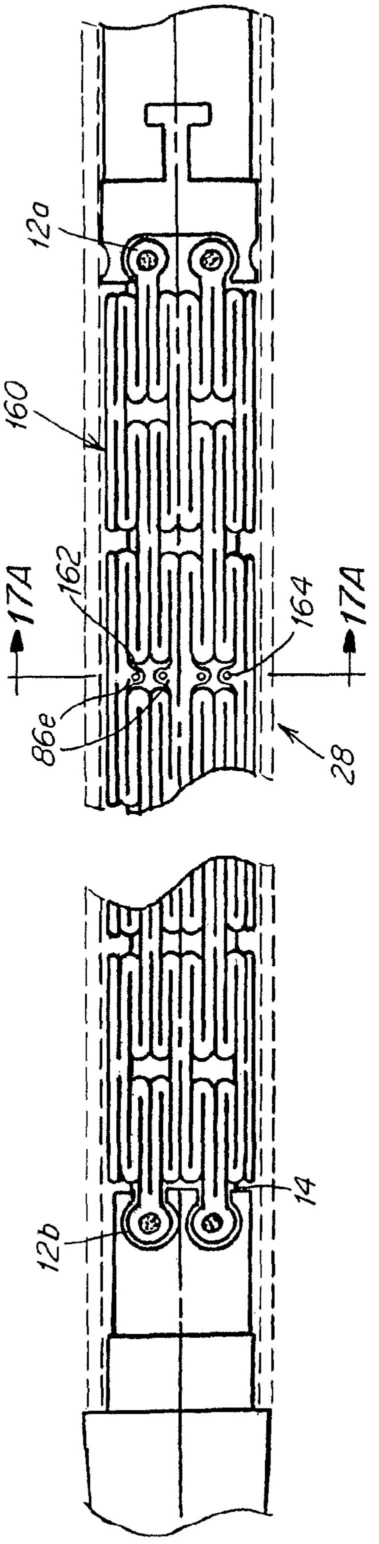
FIGS. 17, 18, 19 and 20 are enlarged views of the distal ends of embodiments of stent delivery systems having inventive aspects in accordance with the principles of the present disclosure with outer sheaths shown in phantom line.
Figure 17A:
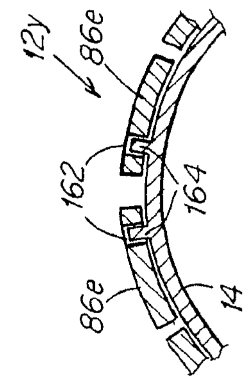
FIGS. 17A, 18A, 19A and 20A are cross sections of portions of the stent systems illustrated in FIGS. 17, 18, 19 and 20, respectively.

FIGS. 17 and 17A illustrate an alternative embodiment of stent mid interlock geometry 28. Stent 160 is comprised of retainers 12*y* in the form of widened stent struts 86*e* having holes 162 in the widened stent struts 86*e*. One or more pins 164 emanate from inner member 14 and in a one embodiment are integral to and fixedly attached to inner member 14. For example, pin 164 can be bonded, crimped, swaged, affixed, fastened, fused, molded in, embedded in, or otherwise secured to inner member 14. When stent 160 is compressed onto inner member 14 pins 164 are inserted into holes 162 and axial motion of stent 160 relative to inner member 14 is prevented thereby. In some embodiments mid interlock geometry 28 is applied to stent 12 and inner member 14 in between proximal end 12*a* and distal end 12*b* of stent 12 at one or more locations along the length of the stent. FIGS. 17 and 17A illustrate pins 164 and holes 162 in an interlocked configuration. When stent is expanded holes 162 move away radially from inner member 14 thereby removing pins 164 from holes 162 and releasing interlock 28.

Figure 18:
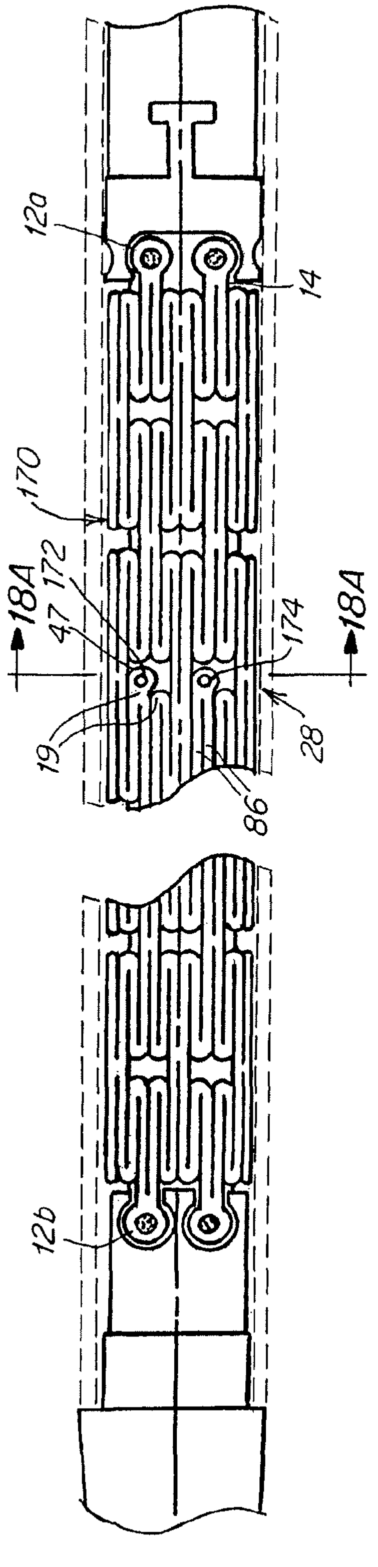
Figure 18A:
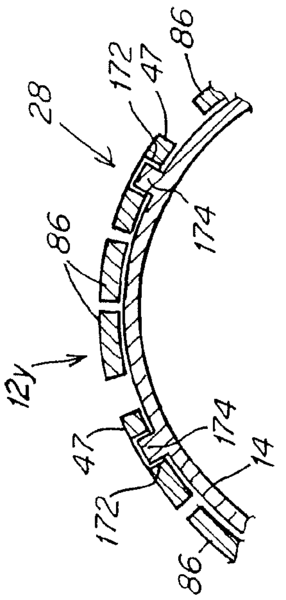

FIGS. 18 and 18A illustrate an alternative embodiment of stent mid interlock geometry 28. Stent 170 is comprised of retainers 12*y* in the form of one or more bend regions 19 having enlarged ends 47 with holes 172. One or more pins 174 emanate from inner member 14 and in, a one embodiment, are integral to and fixedly attached to inner member 14. For example, pin 174 can be bonded, crimped, swaged, affixed, fastened, fused, molded in, embedded in, or otherwise secured to inner member 14. When stent 170 is compressed onto inner member 14 pins 174 are inserted into holes 172 and axial motion of stent 170 relative to inner member 14 is prevented thereby. In some embodiments mid interlock geometry 28 is applied to stent 12 and inner member 14 in between proximal end 12*a* and distal end 12*b* of stent 12 at one or more locations along the length of the stent. FIGS. 18 and 18A illustrate pins 174 and holes 172 in an interlocked configuration. When stent is expanded holes 172 move away radially from inner member 14 thereby removing pins 174 from holes 172 and releasing interlock 28.

Figure 19:
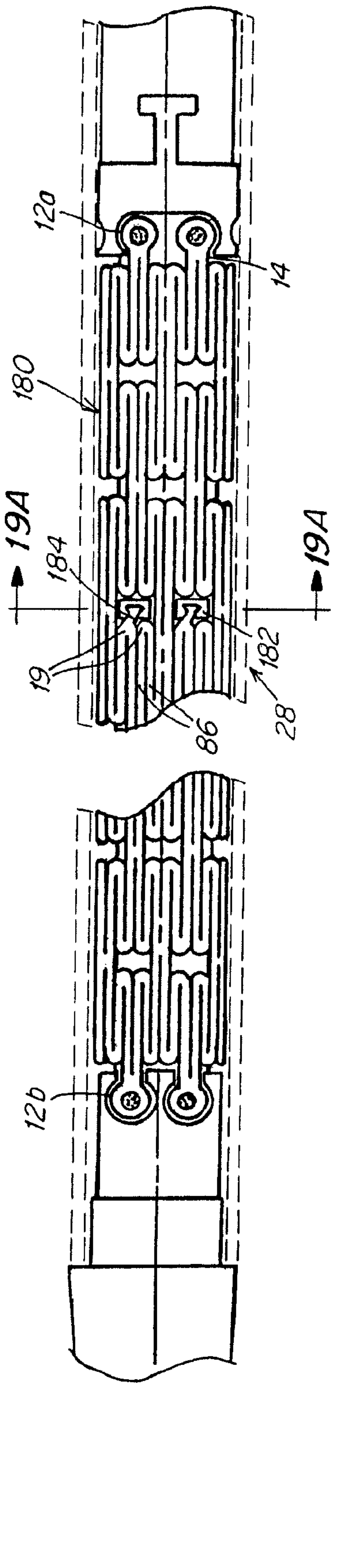
Figure 19A:
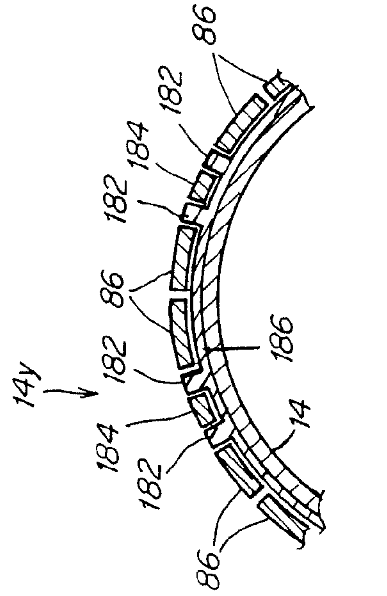

FIGS. 19 and 19A illustrate an alternative embodiment of stent mid interlock geometry 28. Stent 180 is comprised of retainers 14*y* in the form of one or more pockets in interlock band 186. Interlock band is preferably comprised of metal having machined, etched, formed, or stamped pockets, although other constructions are possible, as is known in the art. Stent bend regions 19 may have extended ends 184 with angled geometry that interlocks with retainer pockets. In a one embodiment interlock band 186 is fixedly attached to inner member 14. For example, band 186 can be bonded, crimped, swaged, affixed, fastened, fused, molded in, embedded in, or otherwise secured to inner member 14. When stent 180 is compressed onto inner member 14 extended ends 184 with angled geometry are inserted into retainers 14*y* having pockets in interlock band 186 and axial motion of stent 180 relative to inner member 14 is prevented thereby. In some embodiments mid interlock geometry 28 is applied to stent 12 and inner member 14 in between proximal end 12*a* and distal end 12*b* of stent 12 at one or more locations along the length of the stent. FIGS. 19 and 19A illustrate extended ends 184 and retainers 14*y* having pockets in an interlocked configuration. When stent is expanded ends 184 move away radially from inner member 14 thereby removing ends 184 from retainers 14$y$ having pockets and releasing interlock 28.

Figure 20:
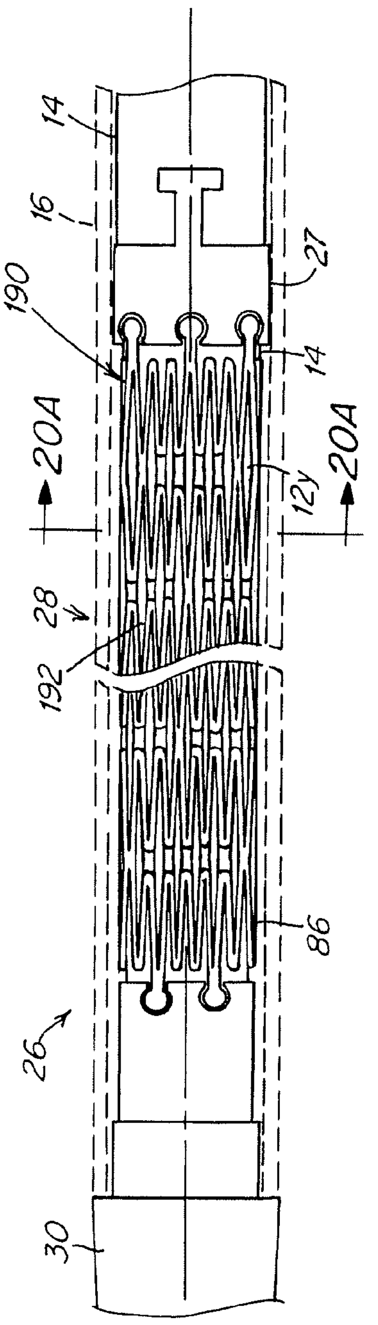
Figure 20B:
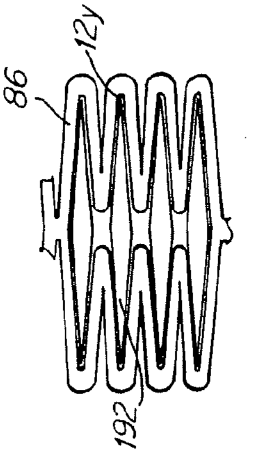
FIG. 20B is a plan view of a portion of the stent system illustrated in FIG. 27.
Figure 20A:
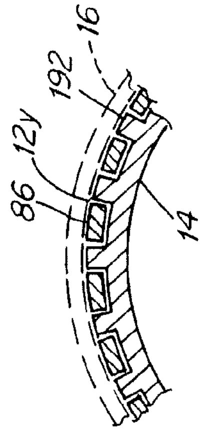

FIGS. 20, 20A and 20B illustrate an alternative embodiment of stent mid interlock geometry 28. Stent 190 is comprised of retainers 12$y$ in the form of spaces between compressed stent struts 86. One or more ridges 192 emanate from inner member 14 and in a one embodiment are integral to and fixedly attached to inner member 14. For example, ridge 192 can be bonded, crimped, swaged, affixed, fastened, fused, molded in, embedded in, or otherwise secured to inner member 14. When stent 190 is compressed onto inner member 14 ridges 192 are inserted into spaces between compressed stent struts 86 and axial motion of stent 190 relative to inner member 14 is prevented thereby. In some embodiments mid interlock geometry 28 is applied to stent 12 and inner member 14 in between proximal end 12$a$ and distal end 12$b$ of stent 12 at one or more locations along the length of the stent. FIGS. 20, 20A and 20B illustrate ridges 192 and spaces between compressed stent struts 86 in an interlocked configuration. When stent is expanded spaces between compressed stent struts 86 move away radially from inner member 14 thereby removing ridges 192 from spaces between compressed stent struts 86 and releasing interlock 28.

Figure 21:
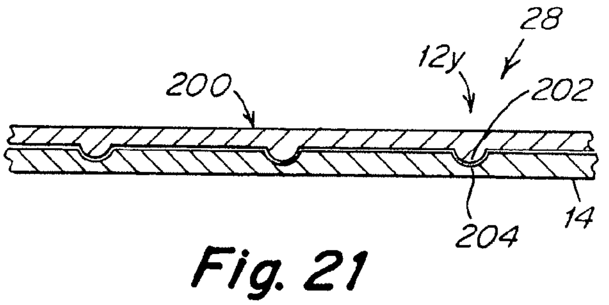
FIGS. 21 and 22 are cross sections of portions of stent delivery systems having inventive aspects in accordance with the principles of the present disclosure.
Figure 21A:
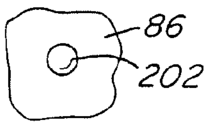
FIGS. 21A and 22A are plan views of portions of the stent delivery systems illustrated in FIGS. 21 and 22, respectively.

FIGS. 21 and 21A illustrate an alternative embodiment of stent mid interlock geometry 28. Stent 200 is comprised of retainers 12$v$ in the form of one or more bumps 202 on stent struts 86 and in a one embodiment are integral to and fixedly attached to stent struts 86. For example, bump 202 can be bonded, crimped, swaged, affixed, fastened, fused, molded in, embedded in, or otherwise secured to stent strut 86. Inner member 14 is comprised of one or more divots 204 When stent 200 is compressed onto inner member 14 bumps 202 substantially fill divots 204 and axial motion of stent 200 relative to inner member 14 is prevented thereby. In some embodiments mid interlock geometry 28 is applied to stent 12 and inner member 14 in between proximal end (not shown) and distal end (not shown) of stent 200 at one or more locations along the length of the stent. FIGS. 21 and 21A illustrate bumps 202 and divots 204 in an interlocked configuration. When stent is expanded bumps 202 move away radially from inner member 14 thereby removing bumps 202 from divots 204 and releasing interlock 28.

Figure 22:
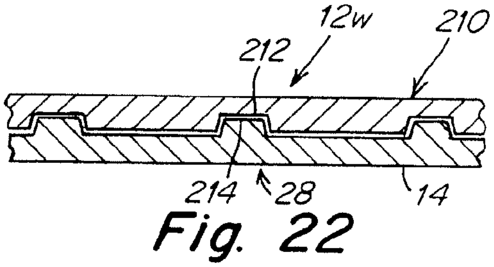
Figure 22A:
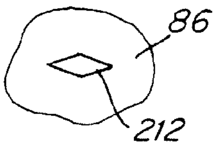

FIGS. 22 and 22A illustrate an alternative embodiment of stent mid interlock geometry 28. Stent 210 is comprised of retainers 12$w$ in the form of one or more cavities 212 on stent struts 86. Inner member 14 is comprises d of one or more mesa's 214 and in a one embodiment mesa's 214 are integral to and fixedly attached to inner member 14. For example, mesa's 214 can be bonded, crimped, swaged, affixed, fastened, fused, molded in, embedded in, or otherwise secured to inner member 14. When stent 210 is compressed onto inner member 14 mesa's 214 substantially fill cavities 212 and axial motion of stent 210 relative to inner member 14 is prevented thereby. In some embodiments mid interlock geometry 28 is applied to stent 12 and inner member 14 in between proximal end (not shown) and distal end (not shown) of stent 210 at one or more locations along the length of the stent. FIGS. 22 and 22A illustrate mesa's 214 and cavities 212 in an interlocked configuration. When stent is expanded mesa's 214 move away radially from inner member 14 thereby removing mesa's 214 from cavities 212 and releasing interlock 28.

An exemplar method of loading a stent having interlock structure that interlocks with interlock geometry of a delivery catheter into a stent delivery system is now described. With reference to the 1, 2, 3, 9, 9A, 6A and 6B self expanding stent 12 comprised of Nitinol and having interlock structure is compressed in an iris style stent compaction machine from an expanded diameter to a contracted diameter. A stent loading tube having a slightly larger internal diameter than that of sheath 16, 66 of stent delivery catheter 10, 60 is slid over stent 12 by repeatedly extending a portion of the stent out of the end of the iris crimper and then sliding the stent loading tube over the extended stent portion. The stent is covered by the loading tube except for the distal interlock structure 26 which is left projecting outside of the end of the loading tube. Next, the inner member 14, 64 of stent delivery catheter 10, 60 having interlock structure is extended outside of sheath 16, 66 of said stent delivery catheter and the compressed stent in loading tube is slid over inner member 14, 64. Distal stent and stent delivery catheter interlocks are connected and the loading tube is slid over the connected distal interlocks to expose proximal interlock structure 27 of the stent 12. Proximal stent and stent delivery catheter interlocks are connected and the sheath is slid over the connected proximal interlocks. Repeatedly, the stent loading tube is withdrawn a short distance to expose a portion of the stent and the sheath is advanced to cover the exposed portion. During this process mid interlock structures 28, if used, are connected.

Advancement forces for the sheath and withdrawal forces for the loading tube are reduced during stent loading because the connected interlocks prevent excessive axial motion of the stent and associated diametrical expansion of the stent. Stent length after loading is also close to stent length prior to loading in a system having mid or distal interlocks. In prior art devices without mid or distal interlocks stent length after loading can be as little as 90% of stent length prior to loading. In a one embodiment of a stent system having inventive interlocks, stent length after loading is 95-105% of stent length prior to loading. In another more embodiment of a stent system having inventive interlocks, stent length after loading is 98-102% of stent length prior to loading. In another more embodiment of a stent system having inventive interlocks, stent length after loading is 99-101% of stent length prior to loading.

An exemplary method of using a stent delivery system having interlock structure in a body of a patient is now described. Using techniques well known in the art, a guidewire is percutaneously inserted into a patient's blood vessel and advanced to a region of interest in the patient's body. Using imaging techniques such as fluoroscopy the diseased portion of the vessel is identified and a stent having the correct length and diameter for a treatment site is chosen. With reference to FIGS. 1, 2, 3, 9, 9A, 6A and 6B, self expanding stent delivery system 10, 60 is advanced over the guidewire to the treatment site and by using imaging techniques such as fluoroscopy both ends 12$a$, 12$b$ of stent 12 are positioned at a correct location relative to the treatment site.

Inner member 14, 64 is held stationary and sheath 16, 66 is withdrawn to exposed stent 12. Stent 12 expands into contact with a lumenal wall of the vessel as sheath 16, 66 is withdrawn. Distal interlock 26 prevents stent from shortening due to axial compression when sheath 16, 66 is withdrawn, thereby facilitating deployment of distal end 12$b$ of expanded stent at the correct location and reducing forces required to withdraw sheath 16, 66. Mid interlocks 28 (if used) prevent stent from compressing axially when sheath 16, 66 is withdrawn thereby reducing forces required to withdraw sheath 16, 66. Proximal interlocks 27 secure stent to stent delivery catheter until sheath 16, 66 is withdrawn proximally to stent end 12$a$, thereby reducing forces required to withdraw sheath 16, 66 and facilitating deployment of proximal end 12$a$ of expanded stent at the correct location. After, and optionally, during stent deployment, stent markers 15 are imaged for various reasons including evaluating deployed stent position relative to treatment site, evaluating extent of stent diametrical expansion, and other reasons.

When using a stent delivery system having mid or distal interlocks to deploy a stent in a body of a patient, stent length after deployment is close to stent length prior to deployment. In prior art devices without mid or distal interlocks stent length after deployment can be as little as 90% of stent length prior to deployment, a disadvantage requiring the use of additional stents to treat the treatment area. In various a embodiments, of a stent system having inventive interlocks, stent length after loading may be any of is 95-105% of stent length prior to loading, more preferably 98-102% of stent length prior to loading, or and even more preferably 99-101% of stent length prior to loading.

When using a stent delivery system having mid or distal interlocks to deploy a stent in a body of a patient, the force required to withdraw sheath 16, 66 (stent deployment force) is reduced as compared to prior art devices without mid or distal interlocks. In a various embodiments, a 150 mm stent deployed from a stent delivery system having mid or distal interlocks has may have a stent deployment force of between any of 50 to 600 grams, more preferably 100 to 400 grams, or and even more preferably 100 to 300 grams. In various alternative embodiments, a 200 mm stent deployed from a stent delivery system having mid or distal interlocks may have has a stent deployment force of between any of 50 to 600 grams, more preferably 100 to 400 grams, or and even more preferably 100 to 300 grams.

Following implantation of a stent having proximal, mid, or distal interlock geometry into a patient the patient may return to the implanting physician for a follow-up visit. During follow-up the markers 15 of implanted stent 12 may be imaged using imaging techniques such as fluoroscopy, ultrasound, or magnetic resonance imaging to assess the position of stent 12 relative to the treatment site, to evaluate the expanded diameter of stent 12, or for other reasons.

While the various embodiments of the present invention have related to a stent and a stent delivery system, the scope of the present invention is not so limited. In addition, it will be appreciated that the various aspects of the present invention are also applicable to systems for delivering other types of expandable implants. By way of non-limiting example, other types of expanding implants include anastomosis devices, blood filters, grafts, vena cava filters, percutaneous valves, aneurism treatment devices, or other devices.

It has been shown how the objects of the invention have been attained in an illustrative manner. Modifications and equivalents of the disclosed concepts are intended to be included within the scope of the claims. Further, while choices for materials and configurations may have been described above with respect to certain embodiments, one of ordinary skill in the art will understand that the materials and configurations described are applicable across the embodiments.

What is claimed is:

1. A medical device comprising:

an implant having a proximal end, a distal end, and a self-expanding portion with a constrained diameter d and a constrained length l, each of the proximal and distal ends including a plurality of terminal retaining segments portion extending therefrom; and an implant delivery system including a catheter defining proximal and distal ends, the catheter having an outer sheath slidably disposed about an inner member, the outer sheath at least partially covering the implant and being retractable relative to the inner member to expose the implant;

a mechanism for enabling increases in the constrained length l of the implant when the outer sheath is retracted relative to the inner member, the mechanism including:

a distal interlock structure attached to the inner member for preventing axial movement of the distal end of the implant relative to the inner member when the outer sheath is retracted relative to the inner member, the distal interlock structure including a first retainer defining a plurality of first cavities configured and dimensioned to receive, and interlock with, respective terminal retaining segments of the distal end of the implant; and a proximal interlock structure attached to the inner member for accommodating increases in the length l of the implant when the outer sheath is retracted relative to the inner member, the proximal interlock structure including a second retainer defining a plurality of second cavities configured and dimensioned to retain respective terminal retaining segments of the proximal end of the implant.

2. The medical device of claim 1 wherein the retaining segments at the distal end of the implant each defines a first profile; and wherein the first cavities of the first and retainer each defines a second profile substantially similar to the first profile for restricting axial movement of the implant relative to the inner member while allowing changes in the constrained diameter d of the implant when the outer sheath is retracted relative to the inner member.

3. The medical device of claim 1 wherein the mechanism for enabling increases in the constrained length l of the implant comprises:

at least a portion of the inner member formed of a material able to resist compression forces exerted thereon by the implant.

4. The medical device of claim 1 wherein the mechanism for enabling increases in the constrained length l of the implant comprises:

an inner surface of the outer sheath which frictionally engages at least a part of the implant when the outer sheath moves is retracted relative to the inner member.

5. The medical device of claim 1 wherein the retaining segments at the proximal end of the implant each defines a first profile; and wherein the second cavities of the second retainer each defines a second profile different from the first profile for accommodating increases in the constrained length l of the implant when the outer sheath is retracted relative to the inner member.

6. The medical device of claim 1 wherein the second cavities of the second retainer each defines a channel having a depth D measurable along a common axis of the inner member and the implant; and wherein the depth D is at least equal to any increases in the constrained length l of the implant when the outer sheath is retracted relative to the inner member.

7. A system for delivering a stent within a body lumen, the system comprising:

a catheter including an outer sheath and an inner member, the outer sheath slidably disposed about the inner member, the catheter defining a longitudinal axis and having proximal and distal ends;

a self-expanding stent disposed intermediate the inner member and the outer sheath, the stent having a proximal stent end and a distal stent end, and a plurality of enlarged terminal segments extending from each of the proximal stent end and the distal stent end; and a distal interlock attached to the inner member, the distal interlock including a distal retainer defining a plurality of cavities dimensioned and configured to receive and couple with the terminal segments at the distal stent end of the stent to restrict proximal axial movement of the distal stent end relative to the inner member when the outer sheath is retracted relative to the inner member and towards the proximal end of the stent.

8. The system of claim 7 wherein the terminal segments at the distal stent end each define a first profile; and wherein the cavities of the distal retainer each define a second profile, substantially similar to the first profile of the terminal segments, to effect coupling of the distal stent end with the distal interlock.

9. The system of claim 8 including a proximal interlock attached to the inner member, the proximal interlock structure including a proximal retainer defining a plurality of cavities for retaining the terminal segments at the proximal stent end of the stent.

10. The system of claim 9 wherein the cavities of the proximal retainer each define a third profile different from the first profile for accommodating increases in a constrained length l of the stent when the outer sheath is retracted relative to the inner member.

11. The system of claim 10 wherein the cavities of the proximal retainer each defines a channel having a depth D measurable along a common axis of the inner member and the stent; and wherein the depth D is at least equal to any increases in the constrained length l of the stent when the outer sheath is retracted relative to the inner member.

12. A system for delivering a stent within a body lumen, the system comprising:

a catheter including an inner member and an outer sheath movable relative to the inner member;

a stent including a tubular, self-expanding section, the stent having a proximal end, a distal end and an intermediate segment therebetween, the stent comprising proximal and distal terminal end segments respectively extending from the proximal and distal ends of the stent;

a proximal interlock cooperatively couplable with the proximal end of the stent;

a distal interlock cooperatively couplable to the distal end of the stent, wherein the distal interlock includes a distal retainer defining a plurality of cavities for receiving and interlocking with the distal terminal end segment of the stent, and to prevent movement of the distal end of the stent when the outer sheath is retracted; and an intermediate interlock attached to the inner member, the intermediate interlock dimensioned and configured to cooperatively couple with the intermediate segment of the stent, the intermediate interlock and the end interlock cooperating to prevent premature deployment of the stent when the outer sheath is retracted relative to the inner member.

13. The system of claim 12 wherein the proximal interlock includes a proximal retainer defining a plurality of cavities for retaining the proximal terminal end segments of the stent.

14. The system of claim 13 wherein the cavities of the proximal retainer are each dimensioned and configured to accommodate increases in a constrained length l of the stent when the outer sheath is retracted relative to the inner member.

15. The system of claim 14 wherein the cavities of the proximal retainer each have a depth D measurable along a common axis of the inner member and the stent; and wherein the depth D is at least equal to any increases in the constrained length l of the stent when the outer sheath is retracted relative to the inner member.

16. The system of claim 12 wherein the intermediate interlock includes at least one protrusion extending from the inner member, the stent having at least one recess for accommodating the at least one protrusion in coupling relation therewith.

17. The system of claim 12 wherein the intermediate interlock includes an interlock band.

* * * * *